US012583366B2

(12) United States Patent (10) Patent No.: US 12,583,366 B2
Kowata et al. (45) Date of Patent: Mar. 24, 2026

(54) VEHICLE SEAT

(71) Applicant: TS TECH CO., LTD., Asaka (JP)

(72) Inventors: Kohei Kowata, Shioya-gun (JP);
Katsuya Kawata, Shioya-gun (JP)

(73) Assignee: TS TECH CO., LTD., Asaka (JP)

( * ) Notice: Subject to any disclaimer, the term of this
patent is extended or adjusted under 35
U.S.C. 154(b) by 197 days.

(21) Appl. No.: 18/342,189

(22) Filed: Jun. 27, 2023

(65) Prior Publication Data

US 2023/0339367 A1 Oct. 26, 2023

Related U.S. Application Data

(63) Continuation of application No.
PCT/JP2021/045344, filed on Dec. 9, 2021.

(30) Foreign Application Priority Data

Dec. 28, 2020 (JP) ................................. 2020-219458
Dec. 28, 2020 (JP) ................................. 2020-219459

(51) Int. Cl.
*B60N 2/66* (2006.01)
*A61B 5/00* (2006.01)
(Continued)

(52) U.S. Cl.
CPC .............. *B60N 2/0022* (2023.08); *A61B 5/05*
(2013.01); *A61B 5/6893* (2013.01);
(Continued)

(58) Field of Classification Search
CPC .... B60N 2/0268; B60N 2/667; B60N 2/6671;
B60N 2/6673
See application file for complete search history.

(56) References Cited

U.S. PATENT DOCUMENTS 12,046,365 B2 * 7/2024 Hirao ................... B60N 2/0033
2019/0315255 A1 * 10/2019 Onuma .................... B60N 2/68

FOREIGN PATENT DOCUMENTS

JP 2018161913 A 10/2018
JP 6572973 B2 9/2019
(Continued)

OTHER PUBLICATIONS

Japanese Office Action (with English translation) for Application
No. 2020219458 Dated Nov. 1, 2024.
(Continued)

*Primary Examiner* — Timothy J Brindley
(74) *Attorney, Agent, or Firm* — Dority & Manning, P.A.

(57) ABSTRACT

A vehicle seat includes a seat cushion and a seatback. The
vehicle seat has a plate-shaped pressure-receiving member
configured to receive a load from an occupant seated on the
vehicle seat and a radio wave sensor fixed to the pressure-
receiving member. The radio wave sensor is configured to
acquire information about the occupant by emitting radio
waves toward the occupant and detecting the radio waves
reflected off the occupant. The pressure-receiving member
includes a plurality of first ribs that protrudes from a
backside of the pressure-receiving member, which is a side
facing away from the occupant, in a direction away from the
occupant, and a plurality of second ribs that protrudes from
the backside in a direction away from the occupant, the
plurality of second ribs crossing the plurality of first ribs.
The radio wave sensor includes at least one fixing part that
is fixed to the pressure-receiving member. The at least one
fixing part includes a first fixing part that is fixed to a
surrounded area that is surrounded by the plurality of first
ribs and the plurality of second ribs on the backside.

19 Claims, 14 Drawing Sheets

(51) Int. Cl.

| | | |
|---|---|---|
| *A61B 5/05* | (2021.01) | |
| *B60N 2/00* | (2006.01) | |
| *B60N 2/02* | (2006.01) | |

(52) U.S. Cl.
CPC ......... *B60N 2/0031* (2023.08); *B60N 2/0268* (2023.08); *B60N 2/667* (2015.04); *B60N 2/6673* (2015.04); *B60N 2/66* (2013.01)

(56) References Cited

FOREIGN PATENT DOCUMENTS

| | | | |
|---|---|---|---|
| JP | 2019182274 A | | 10/2019 |
| JP | 2019187953 A | * | 10/2019 |
| JP | 2020124982 A | | 8/2020 |
| JP | 2020131807 A | | 8/2020 |
| WO | WO2017022493 A | | 2/2017 |

OTHER PUBLICATIONS

Japanese Office Action(with English translation) for Application No. 2020219459 Dated Nov. 1, 2024.

PCT International Search Report and Written Opinion (w/ English translation) for corresponding PCT Application No. PCT/JP2021/045344, mailed Feb. 22, 2022, 17 pages.

Chinese Office Action (with English translation) for corresponding Application No. 202180088022.6, dated Jul. 19, 2025, 18 pages.

* cited by examiner

VEHICLE SEAT

REFERENCE TO RELATED APPLICATIONS

This application is a continuation application of International Application No. PCT/JP2021/045344 filed on Dec. 9, 2021 which claims priority from Japanese Patent Application Nos. 2020-219458 and 2020-219459 filed on Dec. 28, 2020. The disclosures of these applications are incorporated herein by reference in their entirety.

TECHNICAL FIELD

The present disclosure relates to a vehicle seat including a seat cushion and a seatback.

BACKGROUND ART

A vehicle seat provided with a plate-shaped pressure-receiving member for receiving a load from the occupant is hitherto known in the art. For example, in a vehicle seat described in JP2019-182274 A, a pressure-receiving member is provided in the seatback, and is configured to be movable rearward when receiving a load from a seated occupant. Also, in a vehicle seat described in JP 6572973 B2, a pressure-receiving member and a support member that supports the pressure-receiving member while deforming the shape of the pressure-receiving member are provided. The support member includes a lower ascent/descent plate, an upper ascent/descent plate that moves upward and downward relative to the lower ascent/descent plate, and a flexible arch member which have an upper end fixed to the upper ascent/descent plate and a lower end fixed to the lower ascent/descent plate, wherein when the upper ascent/descent plate moves toward the lower ascent/descent plate, the arch member bends and juts forward and pushes the pressure-receiving member forward.

DESCRIPTION

Incidentally, recent-year vehicle seats may be provided with a radio wave sensor for detecting heartbeats or respiration of an occupant. When such radio wave sensor is attached to the movable pressure-receiving member as described above, a high attaching rigidity for the radio wave sensor is desired. When the radio wave sensor is provided in the vehicle seat that includes the pressure-receiving member and the support member, placing the radio wave sensor in a positon that does not interfere with the movement of the support member or the pressure-receiving member is also desired.

In consideration of the background described above, a vehicle seat that includes a seat cushion and a seatback is proposed. In one aspect, a vehicle seat includes a pressure-receiving member and a radio wave sensor fixed to the pressure-receiving member. The pressure-receiving member is configured to receive a load from a seated occupant, and includes a plurality of first ribs protruding from a backside of the pressure-receiving member, which is a side facing away from the occupant, in a direction away from the occupant, and a plurality of second ribs protruding from the backside in a direction away from the occupant, the plurality of second ribs crossing the plurality of first ribs. The radio wave sensor emits radio waves toward the occupant and detects radio waves reflected off the occupant to acquire information about the occupant, and includes at least one fixing part that is fixed to the pressure-receiving member, wherein the at least one fixing part includes a first fixing part that is fixed to a surrounded area that is surrounded by the plurality of first ribs and the plurality of second ribs on the backside.

With this configuration, the surrounded area surrounded by the ribs of the pressure-receiving member is a part that is higher in rigidity and harder to deform, and the attaching rigidity of the radio wave sensor may thus be increased by being fixed to the surrounded area.

The radio wave sensor of the above-described vehicle seat may be configured to include a plurality of first fixing parts.

With this configuration, a plurality of parts of the radio wave sensor is fixed to the surrounded area of the pressure-receiving member; therefore the attaching rigidity may be increased.

The pressure-receiving member of the above-described vehicle seat may be configured to have a plurality of surrounded areas and each first fixing part may be fixed to a different surrounded area.

With this configuration, the size of each surrounded area may be reduced; therefore the rigidity of each surrounded area may be increased. By fixing each first fixing part of the radio wave sensor to each surrounded area with high rigidity, the attaching rigidity of the radio wave sensor may be further increased.

In the above-described vehicle seat, the pressure-receiving member may include at least one surrounded area provided at each of the left and right sides of a center equidistance from right and left edges of the pressure-receiving member.

With this configuration, the radio wave sensor may be arranged across the center of the pressure-receiving member in the left-right direction and therefore the weight imbalance of the pressure-receiving member resulting from attachment of the radio wave sensor may be suppressed.

In the above-described vehicle seat, the pressure-receiving member and the radio wave sensor may be provided at the seatback.

In the above-described vehicle seat, the radio wave sensor may be disposed at a lower part of the pressure-receiving member.

With this configuration, a sufficient amount of flexibility of an upper part of the pressure-receiving member may be ensured.

The above-described vehicle seat may be configured to include an attaching wire for attaching the pressure-receiving member to a frame of the vehicle seat. The attaching wire includes a pair of extended parts that extends in a direction perpendicular to a left-right direction, the pair of extended parts supporting the pressure-receiving member. The surrounded area is provided between the pair of extended parts in the left-right direction.

With this configuration, both the left and right side of the surrounded area are supported by the attaching wire; therefore the attaching rigidity of the radio wave sensor may be increased.

In the above-described vehicle seat, the fixing part may be fixed to the pressure-receiving member by a screw.

With this configuration, the radio wave sensor may be attached to the pressure-receiving member relatively easily.

In the above-described vehicle seat, the radio wave sensor is configured to be a sensor that detects at least one of the heartbeats or the respiration of the occupant.

Another aspect of a vehicle seat in which a seat cushion and a seatback are included will be disclosed. This vehicle seat includes a plate-shaped pressure-receiving member that receives a load from an occupant seated, a support member that supports the pressure-receiving member from a side thereof facing away from the occupant, wherein the support member deforms the shape of the pressure-receiving member, and a radio wave sensor that acquires information about the occupant by emitting radio waves toward the occupant and detecting the radio waves reflected off the occupant. The support member includes a first plate-shaped member, a second plate-shaped member that moves toward or away from the first plate member in a perpendicular direction that is perpendicular to a left-right direction, and a flexible arch member which has one end fixed to the first plate-shaped member and another end fixed to the second plate-shaped member, wherein the arch member being configured to bend and jut out toward the occupant side and push the pressure-receiving member toward an occupant side when the second plate-shaped member moves toward the first plate-shaped member. The pressure-receiving member includes a center portion so located in a center thereof in the left-right direction as to be pressed by the arch member and a left and right side portions located respectively at left and right sides of the center portion, wherein the radio wave sensor is attached to a side portion.

With this configuration, the radio wave sensor may be placed in such a positon as not to interfere with the movement of the support member or the pressure-receiving member.

In the above-described vehicle seat, the radio wave sensor may be configured to be attached to a side, facing away from the occupant side, of the side portion.

With this configuration, the discomfort the occupant may feel from the radio wave sensor when the occupant is seated on the vehicle seat may be suppressed.

In the above-described vehicle seat, each of the side portions may extend in an obliquely forward and laterally outward direction from each of the left and right ends of the center portion so that the side portions extend forward as the side portions extend laterally outward.

With this configuration, the radio wave sensor may be more easily disposed to face the occupant.

In the above-described vehicle seat, the side portions include a first side portion and a second side portion. The first side portion has a shape of an elongated plate of which a width in the perpendicular direction is shorter than a length in the left-right direction. The second side portion includes a plurality of plate-shaped parts, each having an elongated shape of which a width in the perpendicular direction is shorter than a length in the left-right direction, the plurality of plate-shaped parts spaced apart from each other in the perpendicular direction, and a connecting part that connect ends of the plurality of plate-shaped parts, wherein the radio wave sensor is fixed to the second side portion.

With this configuration, a sufficient amount of flexibility of the side portion of the pressure-receiving member may be ensured by the first side portion, while the rigidity of the second side portion to which the radio wave sensor is attached to may be increased; therefore the attaching rigidity of the radio wave sensor may be increased. In other words, ensuring a sufficient amount of flexibility of the pressure-receiving member and increasing the attaching rigidity of the radio wave senor may be compatibly achieved.

The above-described vehicle seat may be configured to have the pressure-receiving member, the support member, and the radio wave sensor provided in the seatback, wherein the second side portion is located at a lower part of the pressure-receiving member.

With this configuration, the discomfort the occupant may feel from the second side portion to which the radio wave sensor is attached, associated with the motion of the support member and the pressure-receiving member, may be suppressed.

In the above-described vehicle seat, the side portion may be configured to have a plurality of plate-shaped parts, each having an elongated shape of which a width in the perpendicular direction is shorter than a length in the left-right direction, the plurality of plate-shaped parts being spaced apart from each other in the perpendicular direction, wherein the radio wave sensor is disposed across the plurality of the plate-shaped parts in the perpendicular direction.

With this configuration, the radio wave sensor may emit and detect the radio waves through between the plate-shaped parts; therefore the radio wave sensor may emit and detect the radio waves without fail.

Another aspect of a vehicle seat including a seat cushion and a seatback will be further disclosed. The vehicle seat includes a plate-shaped pressure-receiving member that receive the load of an occupant, a support member that support the pressure-receiving member from a side away from the occupant and change a shape of the pressure-receiving member, and a radio wave sensor that acquire information about the occupant by emitting radio waves toward the occupant and detecting radio waves reflected off the occupant. The support member includes a first plate-shaped member, a second plate-shaped member that moves toward or away from the first plate member in a perpendicular direction that is perpendicular to a left-right direction, and a flexible arch member which has one end fixed to the first plate-shaped member and another end fixed to the second plate-shaped member, the arch member being configured to bend and jut out toward the occupant and push the pressure-receiving member toward an occupant side when the second plate-shaped member moves toward the first plate-shaped member. The radio wave sensor is attached to a side, facing away from the occupant, of the first plate-shaped member or the second plate-shaped member.

With this configuration, the radio wave sensor may be placed in such a position that the movement of the support member or the pressure-receiving member is not interfered.

The above-described vehicle seat may be provided with a sensor orientation changing mechanism which changes an orientation of the radio wave sensor depending on the position of the radio wave sensor in the perpendicular direction.

With this configuration, the radio wave sensor may be oriented in the appropriate direction regardless of the position of the radio wave sensor in the upper-lower direction, and the detection accuracy of the radio wave sensor may be increased.

In the vehicle seat described above, the pressure-receiving member, the support member, and the radio wave sensor may be provided in the seatback.

In the vehicle seat described above, the radio wave sensor may be configured to be a sensor that detects at least one of the heartbeats or the respiration of the occupant.

The above aspects, other advantages and further features will become more apparent by describing in detail illustrative, non-limiting embodiments thereof with reference to the accompanying drawings, in which.

5

Figure 4:
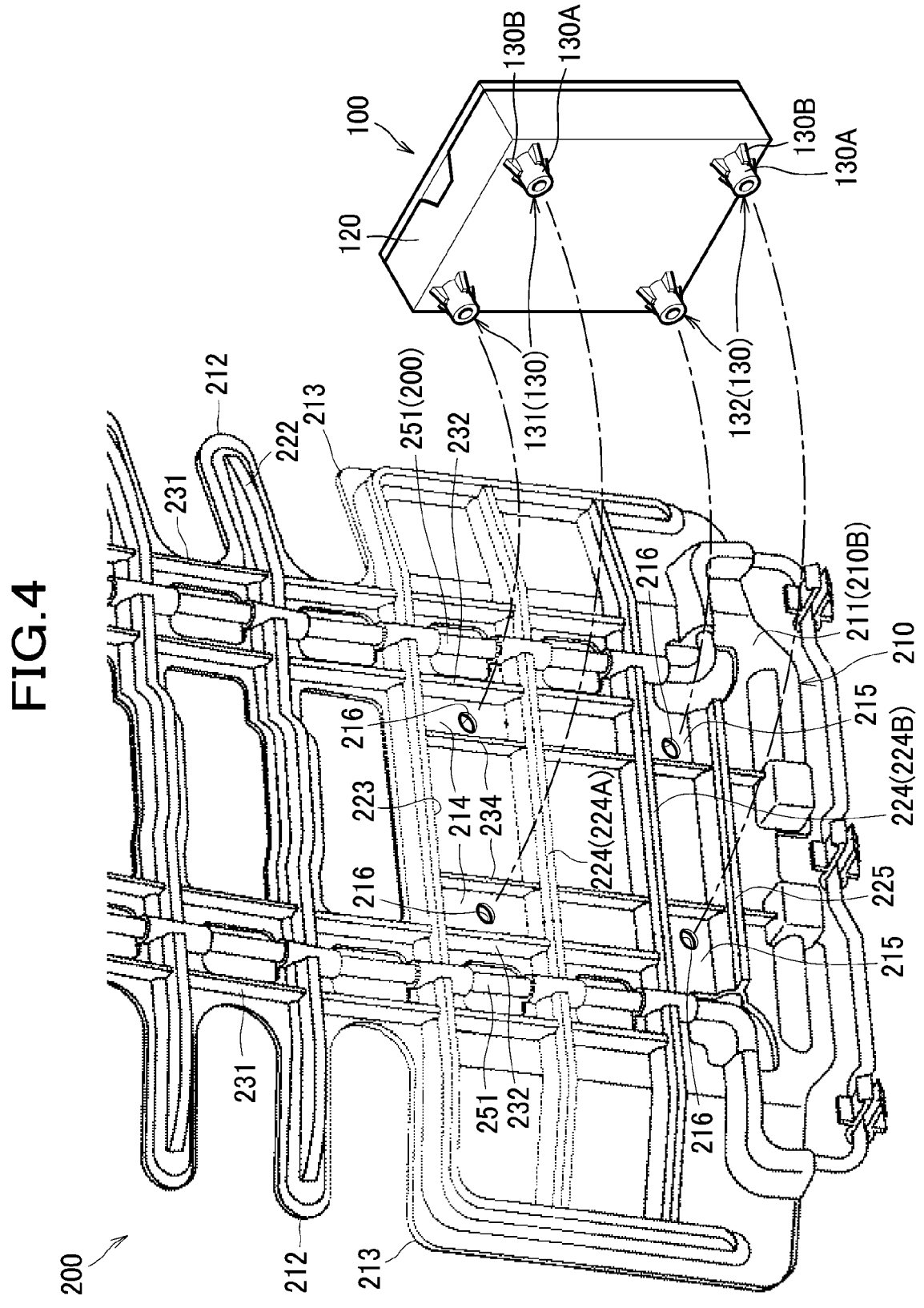

FIG. 4 is a perspective view of a lower part of the pressure-receiving member and a radio wave sensor.

Figure 5:
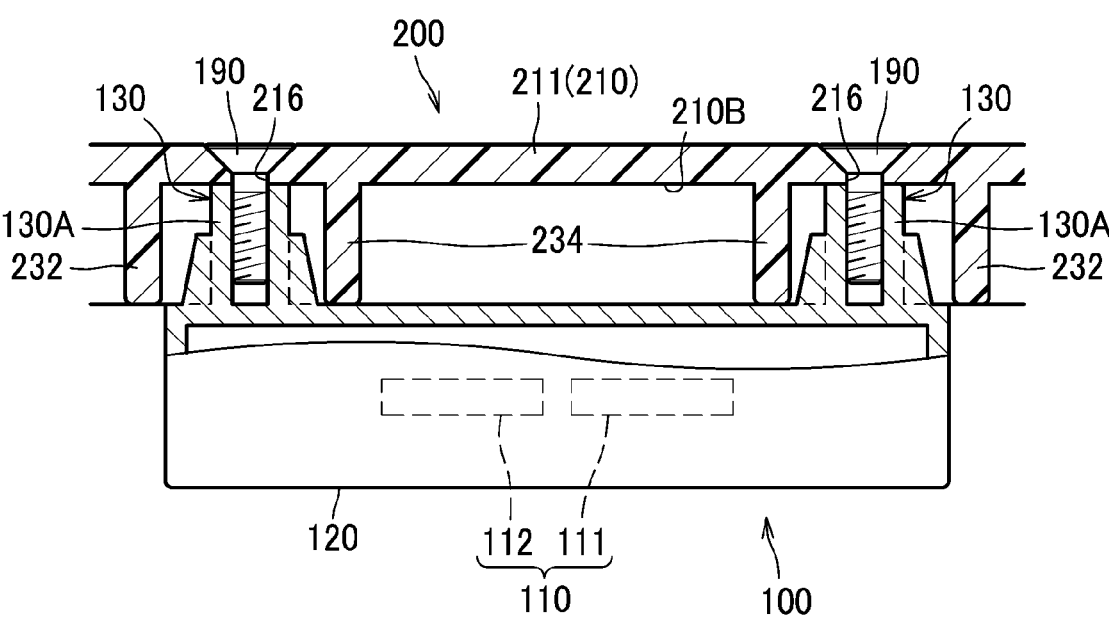

FIG. 5 is a sectional view showing a state in which the radio wave sensor is attached to the pressure-receiving member.

Figure 6:
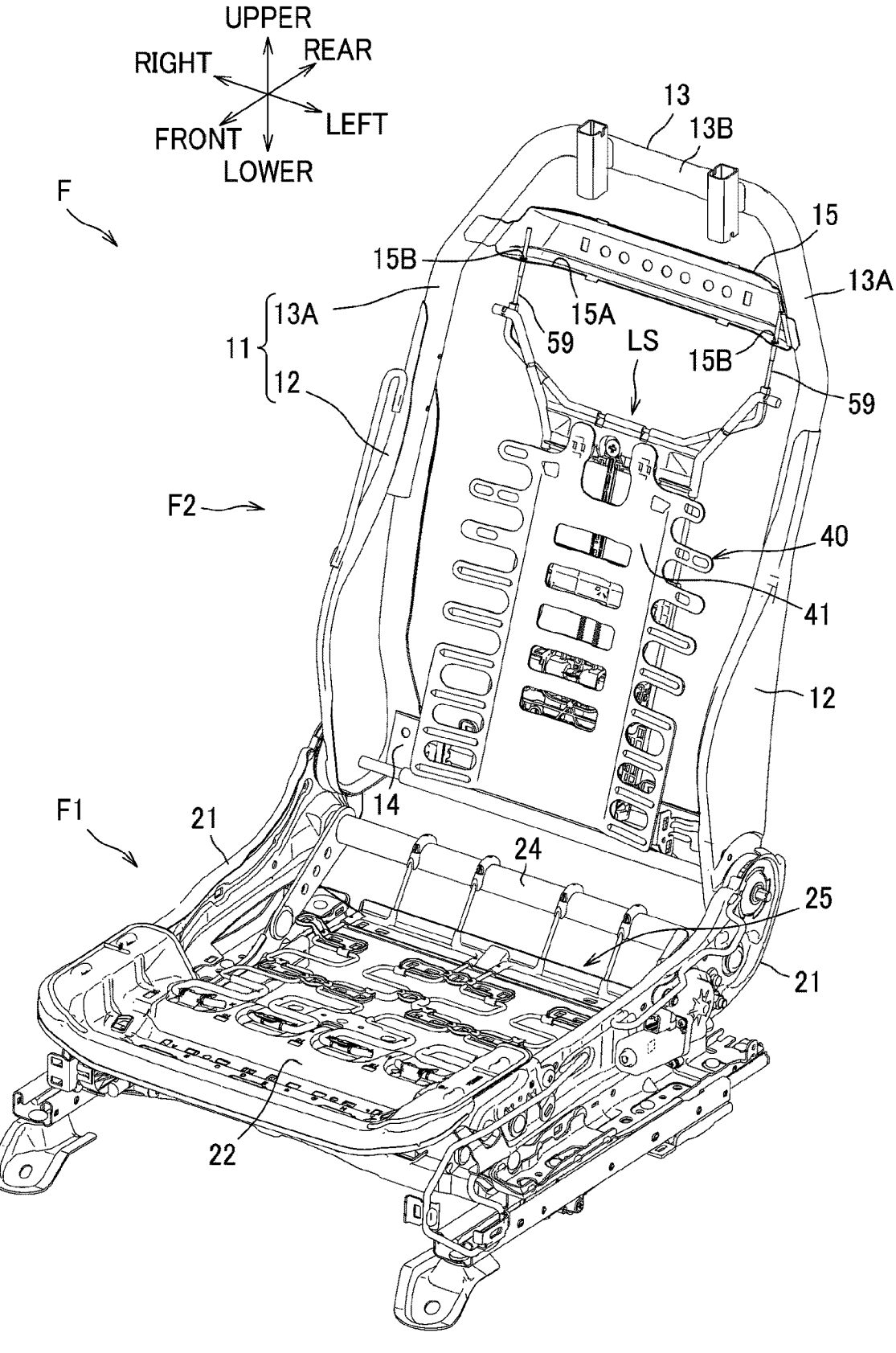

FIG. 6 is a perspective view of a seat frame and a lumbar support device of a vehicle seat according to a second embodiment.

Figure 7:
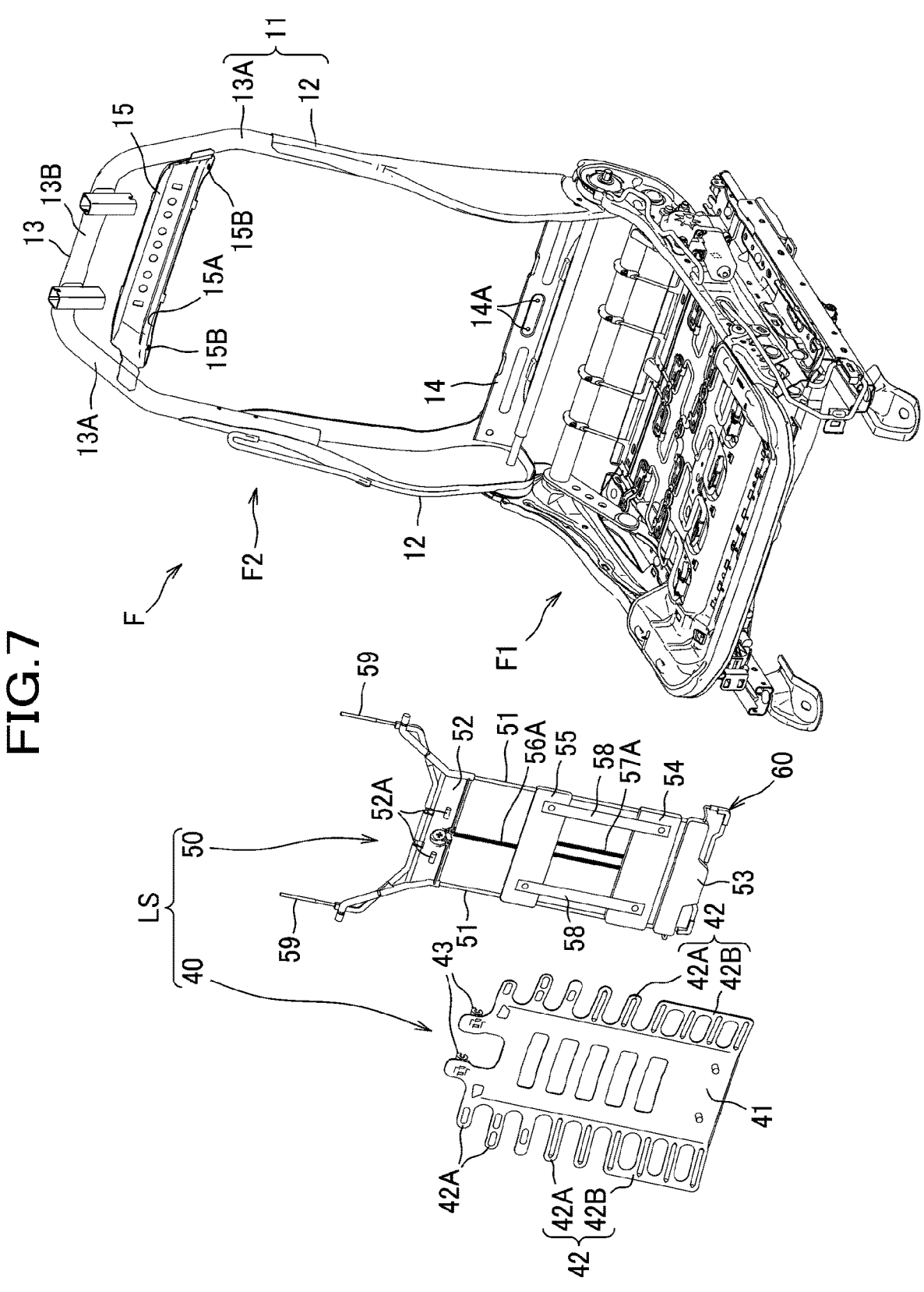

FIG. 7 is a perspective view of a state in which the lumbar support device is detached from the seat frame.

Figure 8:
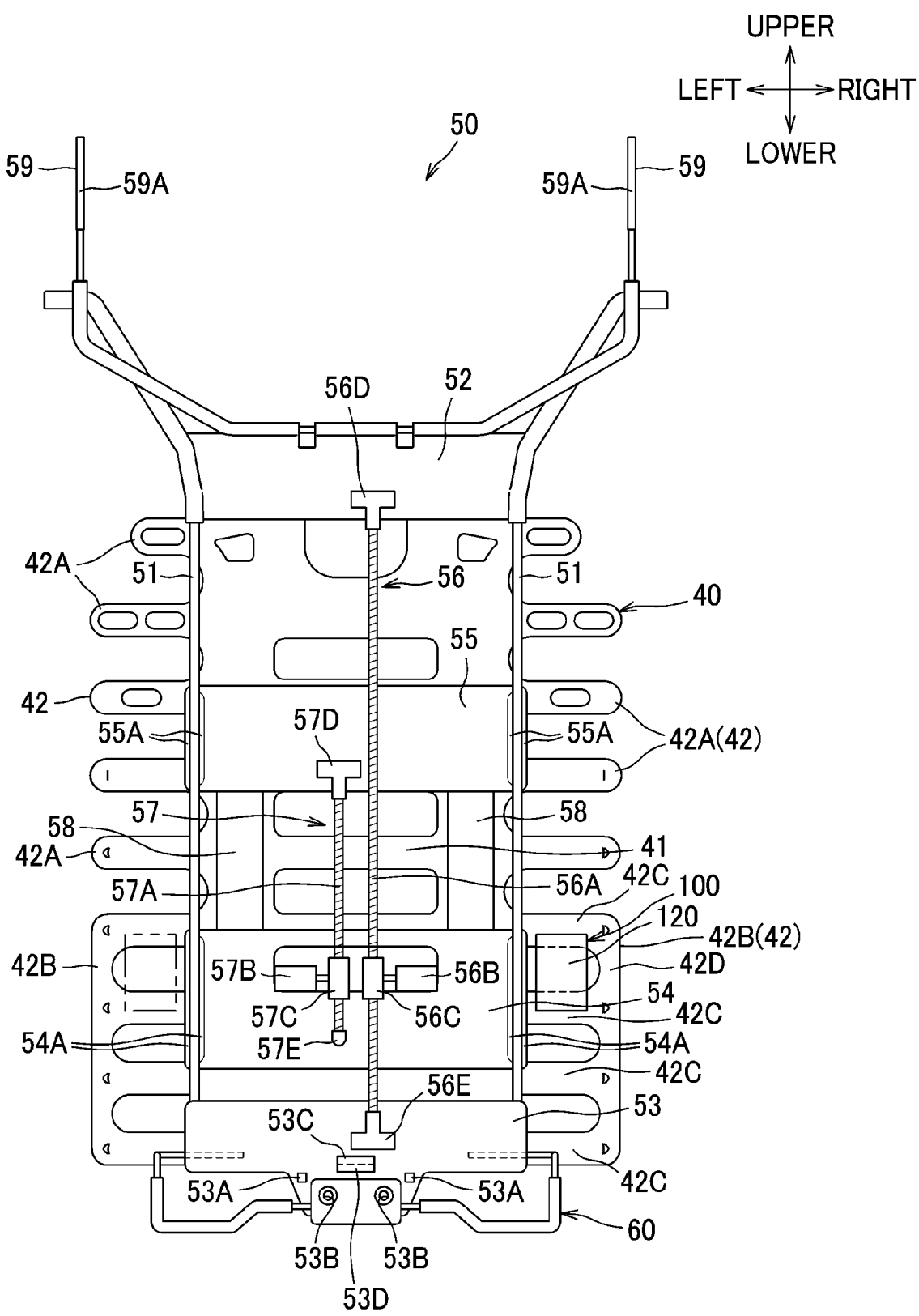

FIG. 8 is a rear view of the lumbar support device.

Figure 9B:
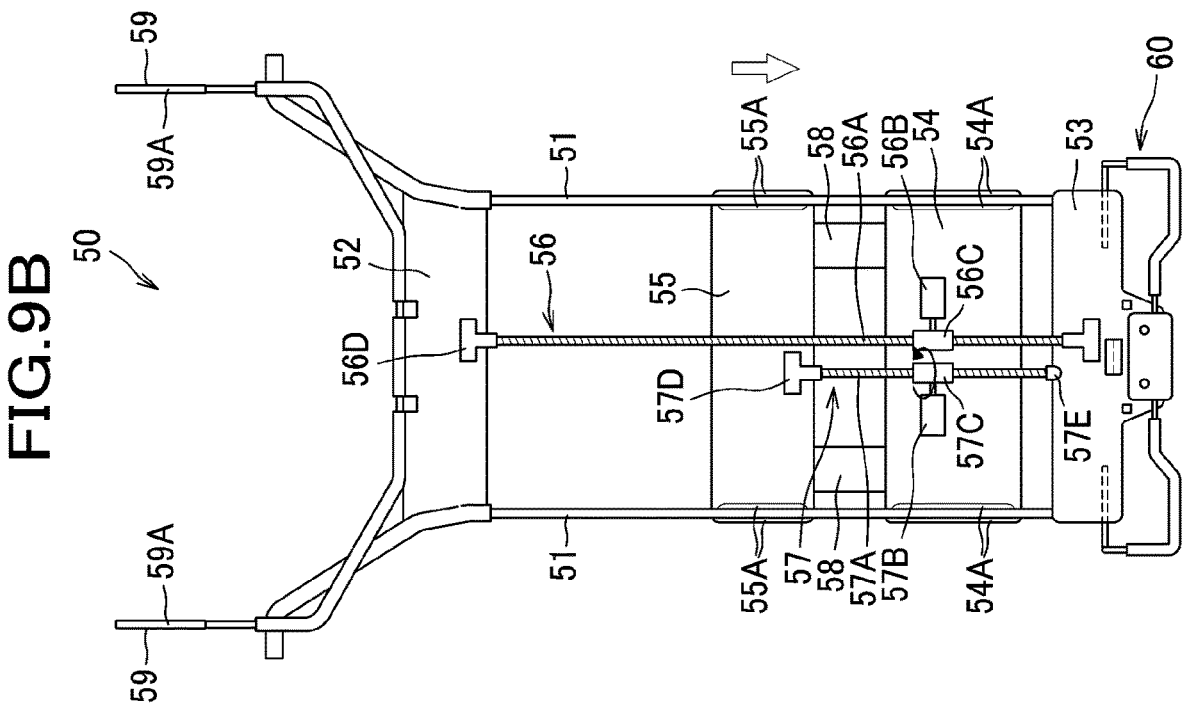
Figure 9A:
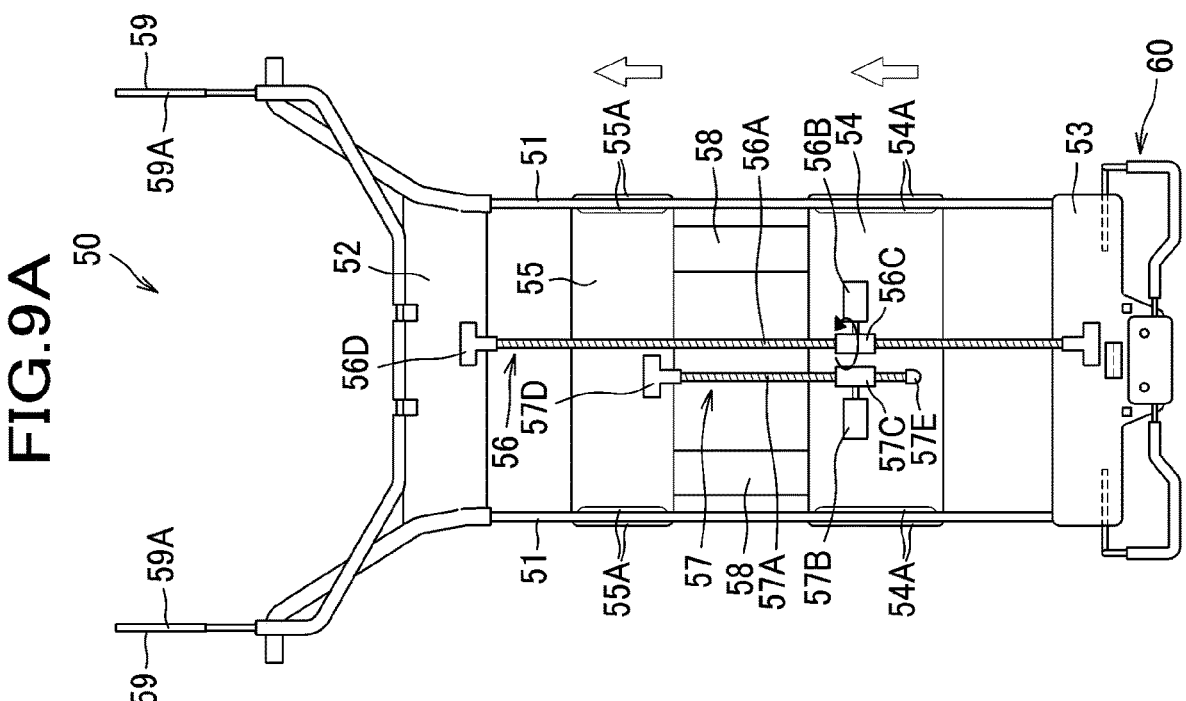

FIG. 9A is a figure that describes the movement of the support member, showing a state in which an upper ascent/descent plate and a lower ascent/descent plate have ascended.

FIG. 9B is a figure that describes the movement of the support member, showing a state in which the upper ascent/descent plate has descended.

Figure 10:
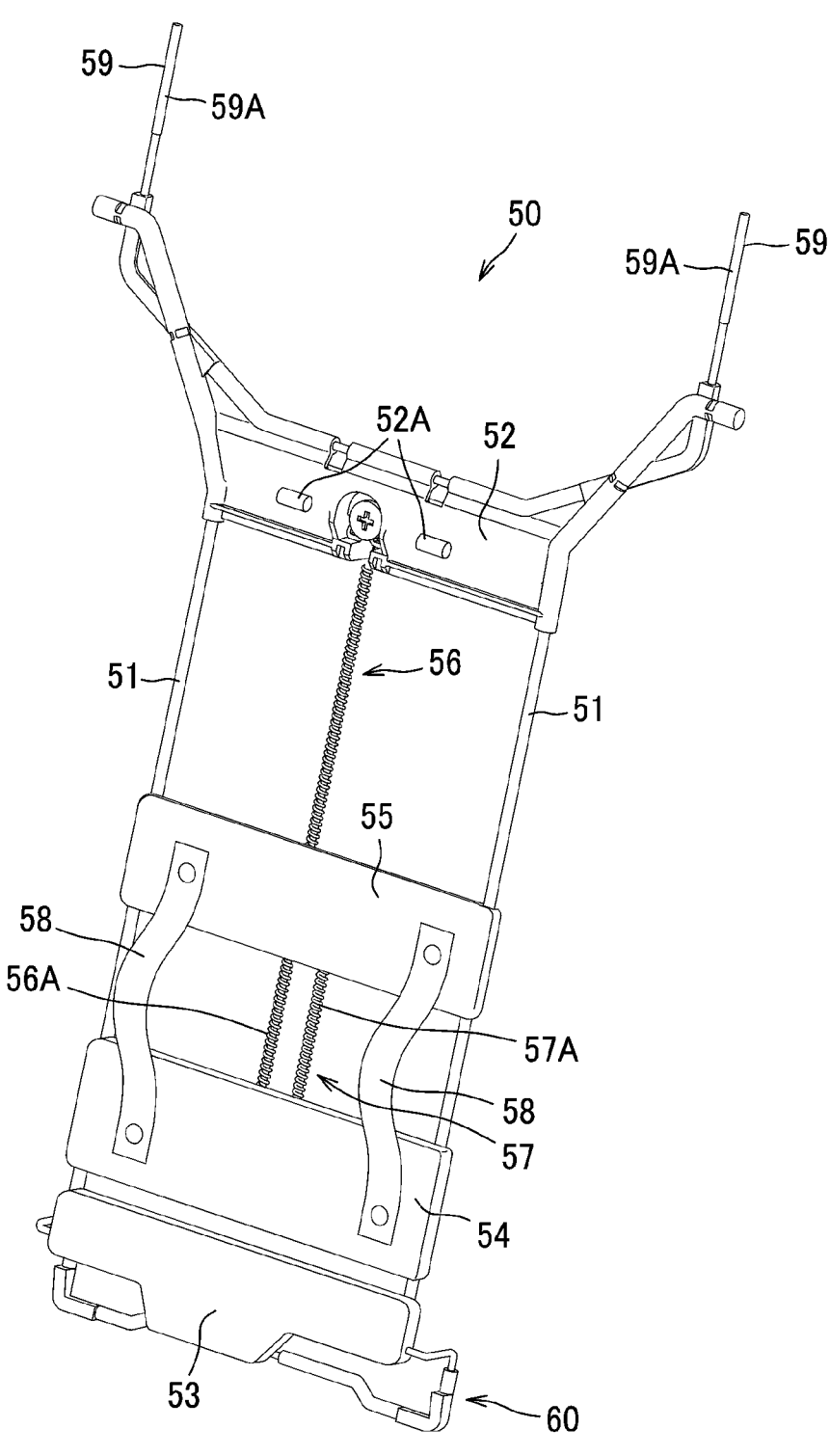

FIG. 10 is a perspective view of the support member when the upper ascent/descent plate has descended and an arch member has bended and jutted forward.

Figure 11:
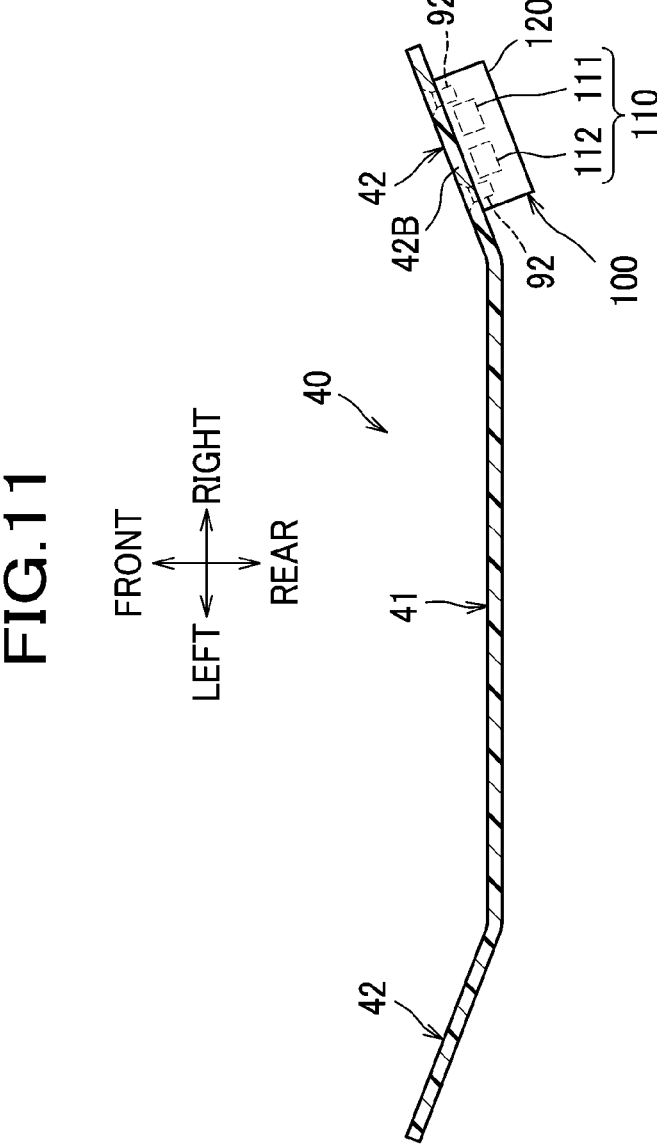

FIG. 11 is a figure that shows the pressure-receiving member and the radio wave sensor.

Figure 12:
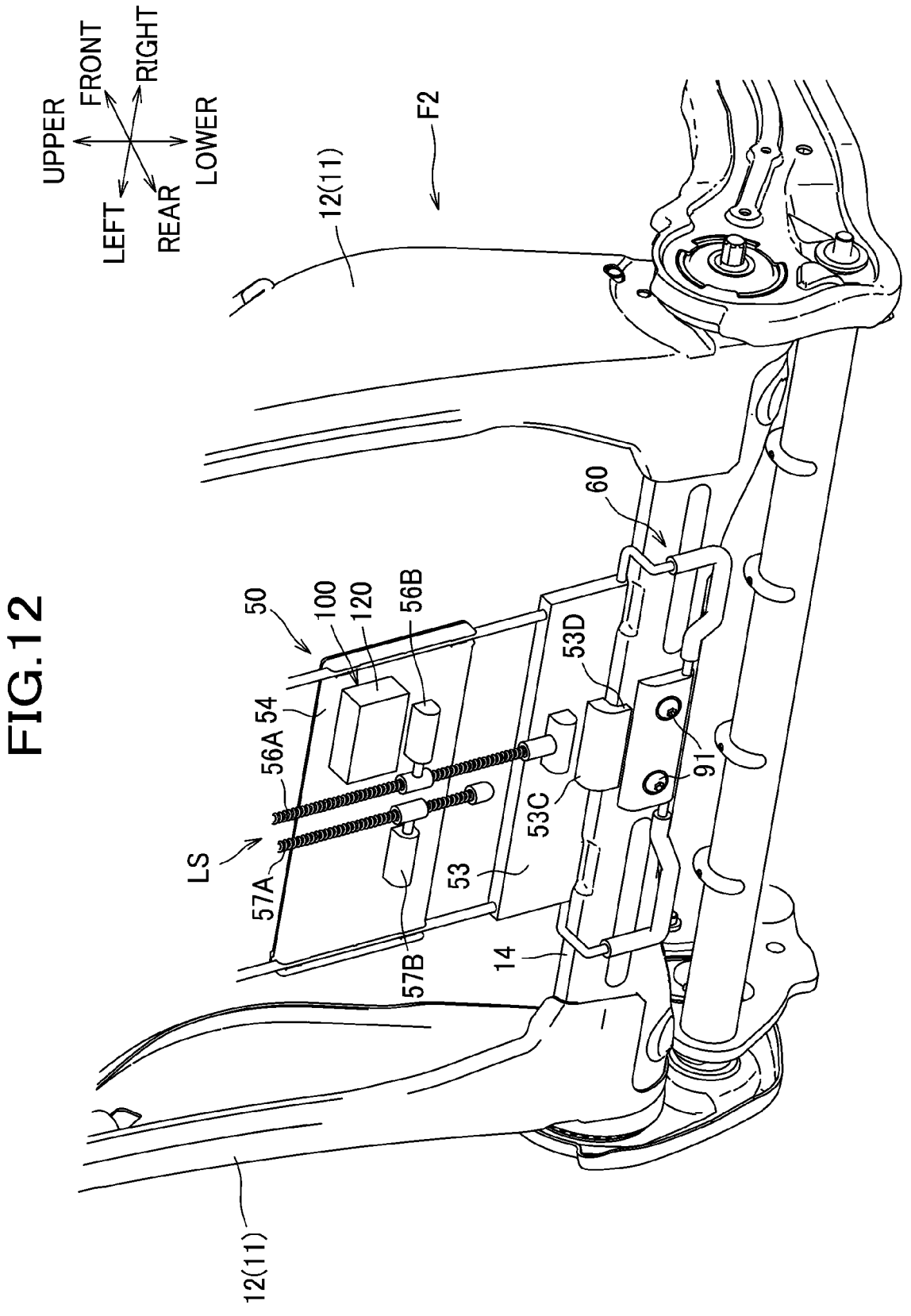

FIG. 12 is a perspective view of a lower part of a seatback frame and a lumbar support device according to a third embodiment, as viewed from the rear side.

Figures 13A, 13B, 13C:
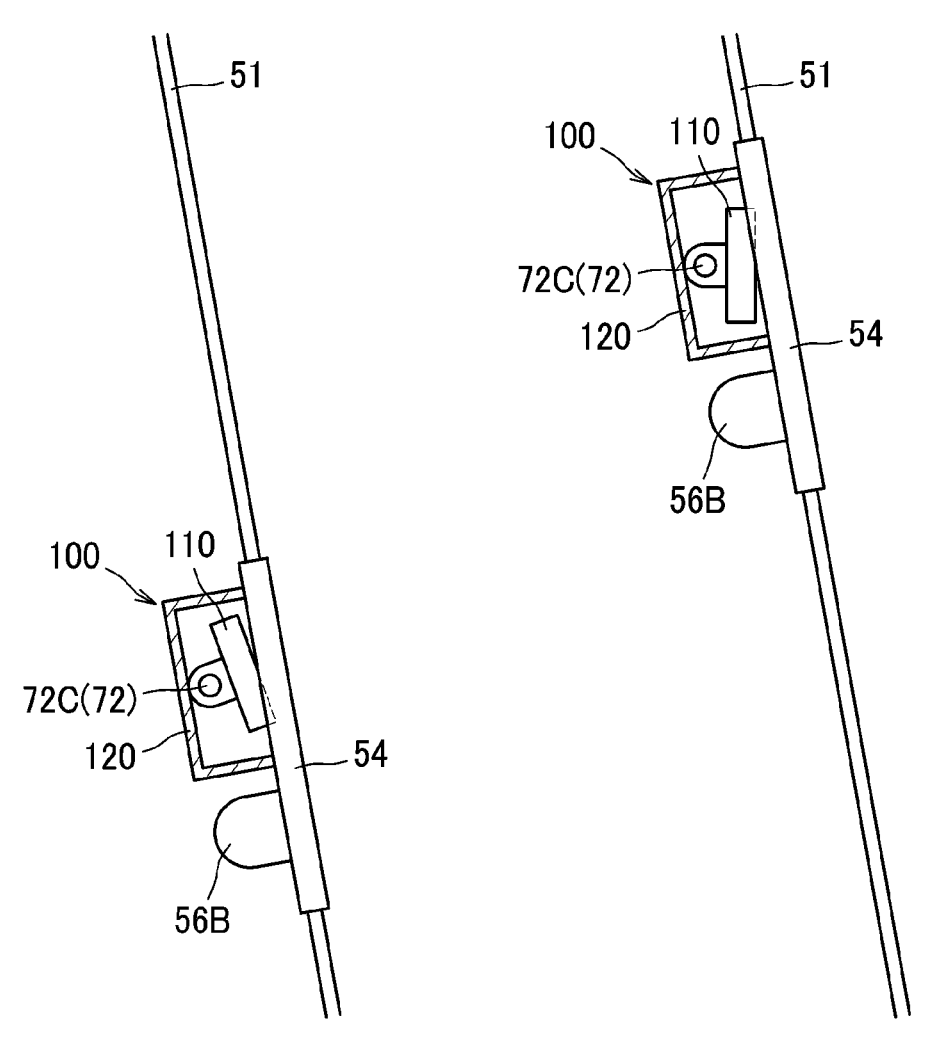

FIG. 13A is a block diagram of a sensor orientation changing mechanism.

FIG. 13B is a figure showing a state in which the lower ascent/descent plate has descended.

FIG. 13C is a figure showing a state in which the lower ascent/descent plate has ascended.

Figure 14:
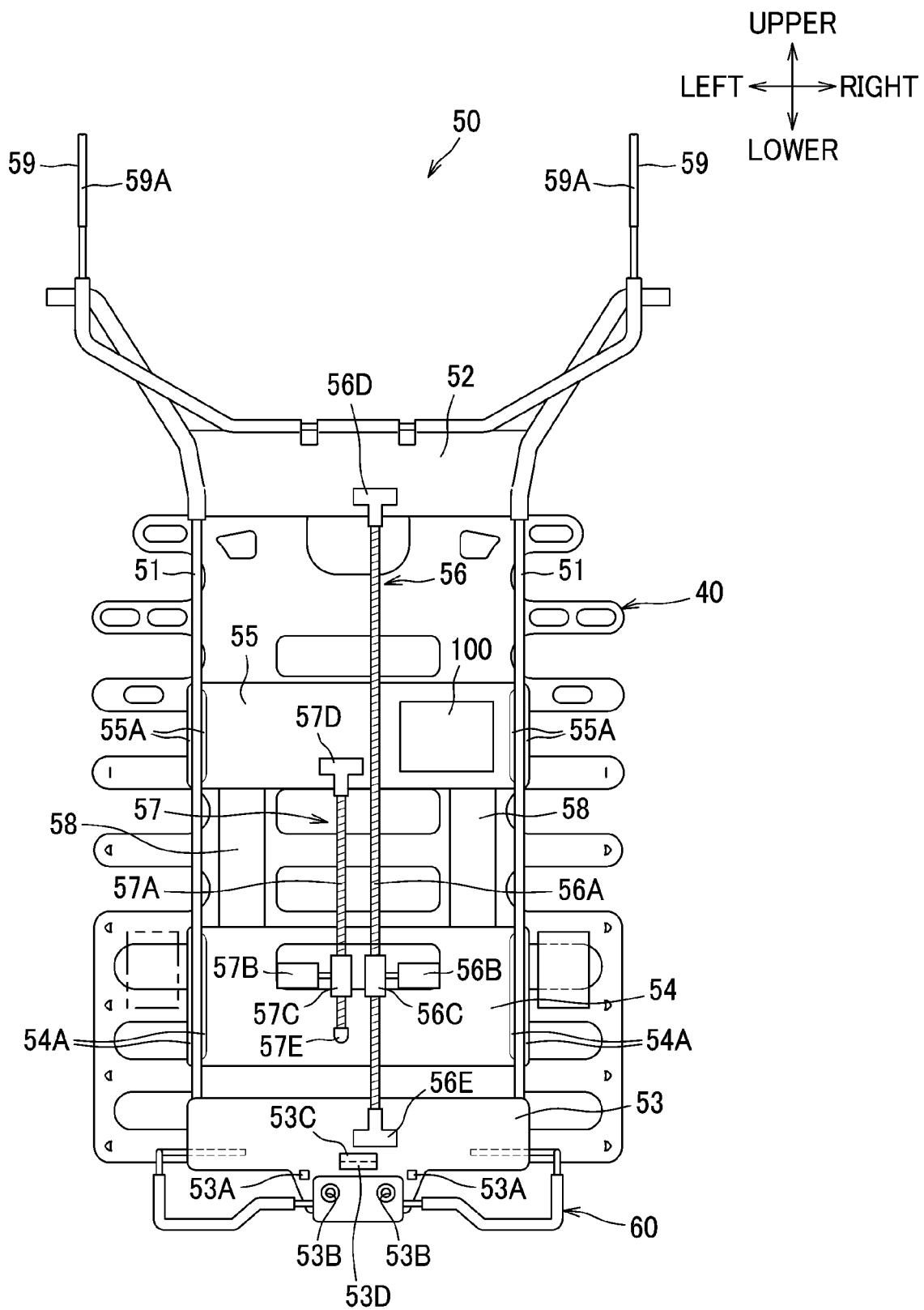

FIG. 14 is a figure showing a modified example of the third embodiment.

Hereafter, a detailed description of a first embodiment will be given with reference made to the drawings where appropriate. In the following description, the front/rear (frontward/rearward), left/right (leftward/rightward; lateral), and up/down (upper/lower; upward/downward; vertical) are represented with reference to the front/rear, left/right, and upper/lower directions as viewed from a person seated on the vehicle seat. In the present embodiment, a front side is the side facing the occupant (the person seated on the seat), a backside is the side facing away from the occupant, and an upper-lower direction is a direction perpendicular to a left-right direction.

Figure 1:
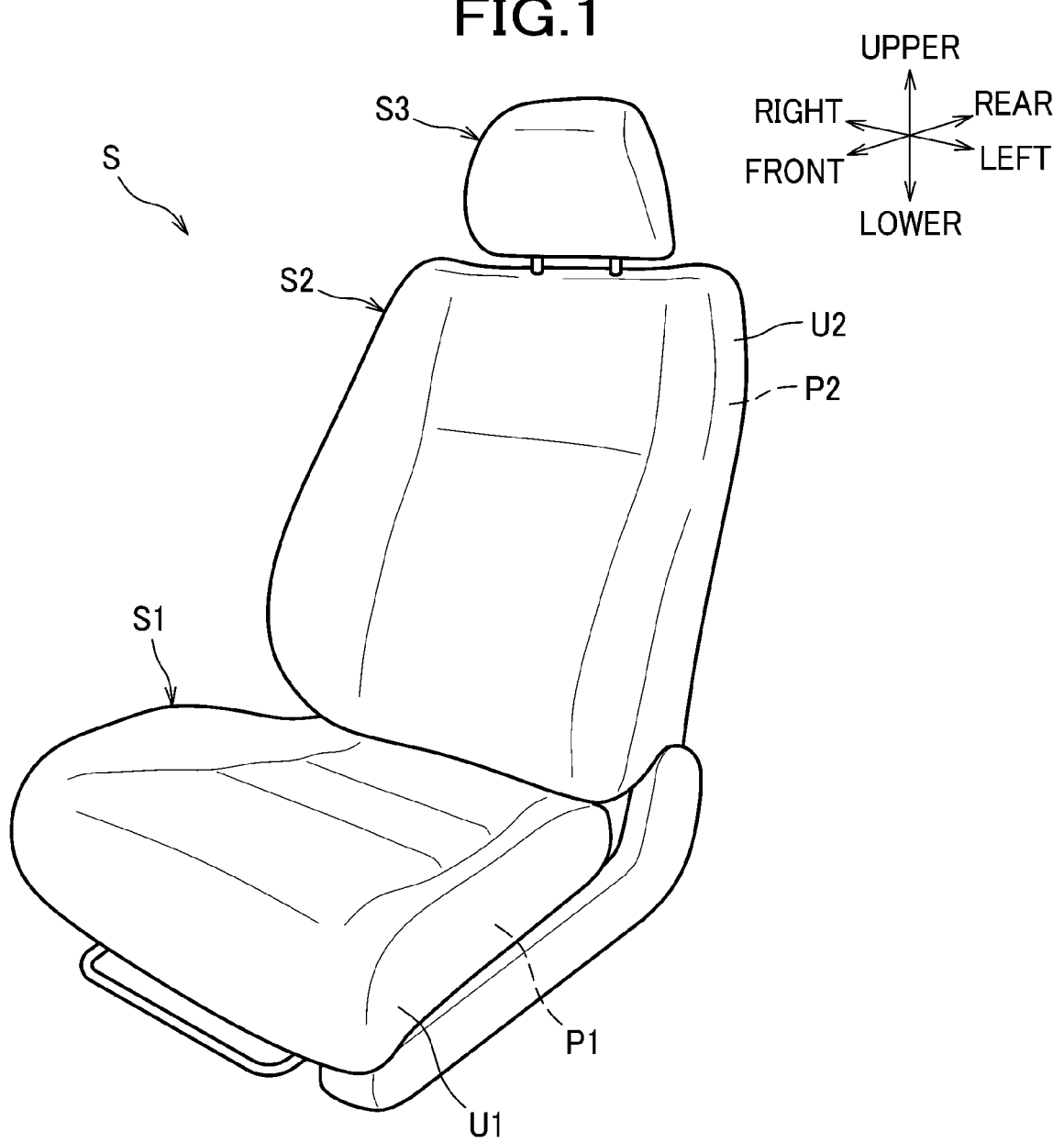
FIG. 1 is a perspective view of a vehicle seat according to the embodiments.

As shown in FIG. 1, a car seat S as an example of the vehicle seat of the present embodiment is configured as a car seat S to be installed in a car such as an automobile. The car seat S is formed by covering a seat frame F (refer to FIG. 2) as a frame of the car seat S with a pad P made of urethane foam or the like and outer coverings made of fabric, leather, etc.

In more detail, the car seat S includes a seat cushion S1, a seatback S2, and a headrest S3. The seat cushion S1 is formed by covering a seat cushion frame F1 (refer to FIG. 2) with a cushion pad P1 and a seat cushion covering U1. The seatback S2 is formed by covering a seatback frame F2 (refer to FIG. 2) with a seatback pad P2 and a seatback covering U2.

Figure 2:
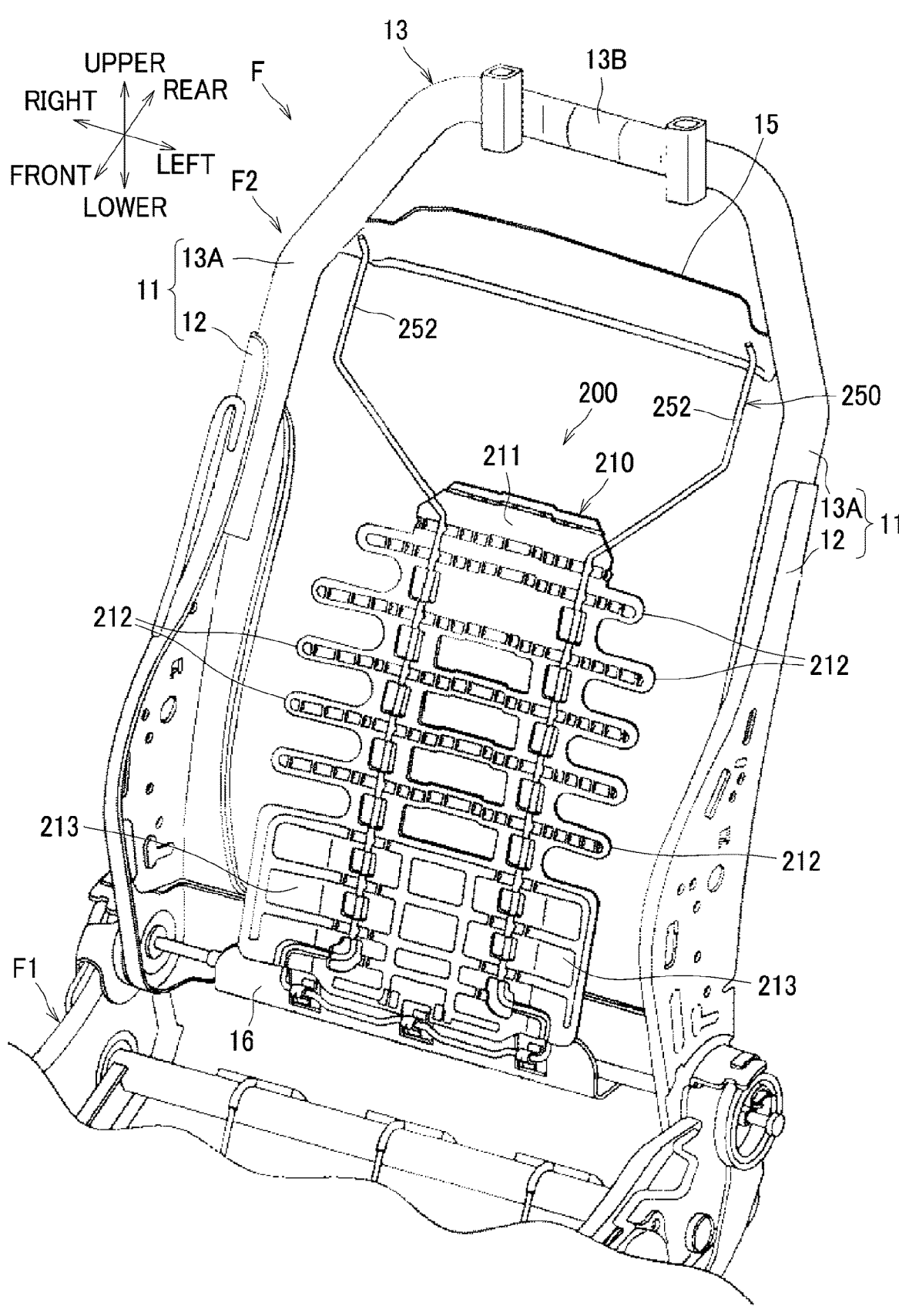
FIG. 2 is a perspective view of a seat frame and a pressure-receiving member of a vehicle seat according to a first embodiment.

As shown in FIG. 2, the seat frame F includes the seat cushion frame F1 and the seatback frame F2. The seatback frame F2 is connected to a rear end portion of the seat cushion frame F1 via a reclining mechanism.

The seatback frame F2 includes a pair of sheet metal frames 12 disposed in laterally separate positions, and a pipe frame 13 made by bending a pipe material into a U-shape and connected to upper ends of the pair of sheet metal frames 12.

The pipe frame 13 includes a pair of left and right upper side frames 13A that extend straight from the sheet metal frames 12 upward to some midpoint and slightly inclined therefrom toward laterally inner sides of the sheet metal frames 12. The left and right sheet metal frames 12 and the upper side frames 13A are a pair of side frames 11 disposed separately to the left and right side. The pipe frame 13 includes an upper frame 13B that connects the upper ends of the pair of upper side frames 13A, in other words the upper ends of the side frames 11.

The seatback frame F2 also includes a lower frame 16 that connects lower parts of the side frames 11, specifically the lower parts of the sheet metal frames 12, and a bridging frame 15 that connects the upper parts of the side frames 11, specifically the left and right upper side frames 13A, at positions lower than a position of the upper frame 13B.

The lower frame 16 and the bridging frame 15 are members made of sheet metal. The lower frame 16 has an elongated shape long in the left-right direction, with the left and right end portions welded to portions of the left and right sheet metal frames 12 that extend laterally inwards. The bridging frame 15 has an elongated shape long in the left-right direction, and the left and right ends of the bridging frame 15 are welded to the upper side frames 13A.

The vehicle seat S further includes a pressure-receiving member 200, an attaching wire 250, and a plurality of attaching clips 260 (refer to FIG. 3) for attaching the pressure-receiving member 200 to the seatback frame F2.

The pressure-receiving member 200 is a plate-shaped member that receives a load from the occupant via the seatback pad P2 (refer to FIG. 1) provided at the seatback S2. The pressure-receiving member 200 is made of plastic or other materials. The pressure-receiving member 200 is approximately symmetrical with respect to a line that passes through the center of the pressure-receiving member in the upper-lower direction. The pressure-receiving member 200 includes a pressure-receiving member body 210. The pressure-receiving member body 210 includes, a center portion 211 located at the center of the pressure-receiving member 200 in the left-right direction, and first side portions 212 and second side portions 213 both disposed at each of the left and right sides of the center portion 211.

The center portion 211 supports the occupant's back and lumbar region directly from the rear of the occupant.

The first side portion 212 and the second side portion 213 are arranged to extend from the left and right ends of the center portion 211 in obliquely frontward and laterally outward directions so that the side portions extend forward as the side portions extend laterally outward.

The first side portion 212 is a portion that supports left and right regions of the back of the occupant diagonally from the rear of the occupant. The first side portion 212 includes five narrow plate-shaped parts of which the width in the upper-lower direction is shorter than the length in the left-right direction, and which are spaced apart from each other in the upper-lower direction at each of the left and right sides of the center portion 211.

The second side portion 213 is a portion that supports the lumbar region of the occupant diagonally from the rear of the occupant and is located below the first side member 212. The side member 213 has a plate-shaped part in which the length in the upper-lower direction is longer than the width in the left-right direction, and extends from each of the lower portions of the left and right ends of the center portion 211 in an obliquely frontward and laterally outward direction.

The first side portion 212 and the second side portion 213 are formed to be moderately flexible to receive the side regions of the occupant softly.

Figure 3:
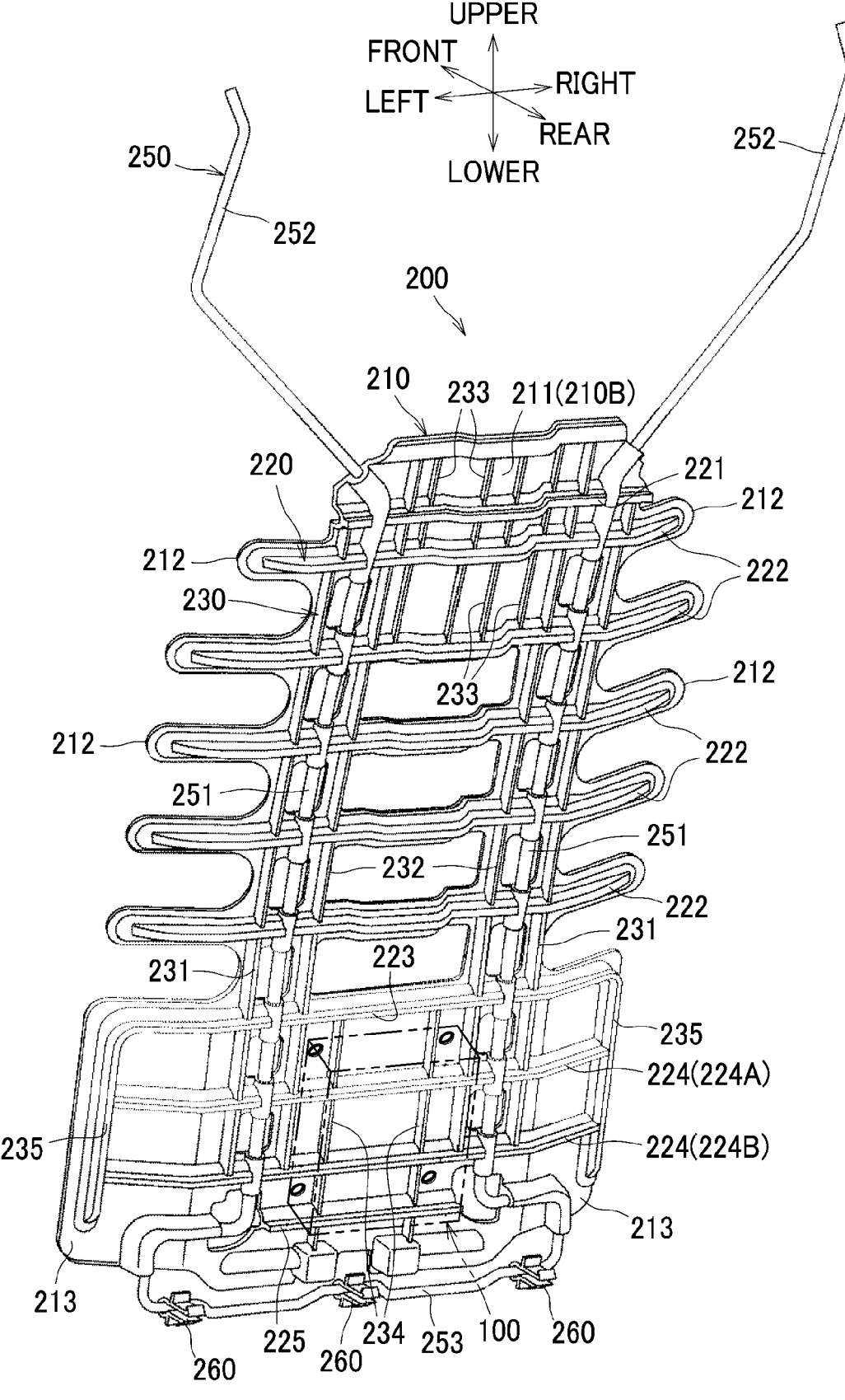
FIG. 3 is a perspective view of the pressure-receiving member as viewed from the rear side.

As shown in FIG. 3, the pressure-receiving member 200 further includes a plurality of lateral ribs 220 and a plurality of longitudinal ribs 230. The lateral ribs 220 and the longitudinal ribs 230 protrude from a backside 210B, which is a rear-side surface of the pressure-receiving member body 210. The lateral ribs 220 extend in the left-right direction and the longitudinal ribs 230 extend in a direction that is perpendicular to the left-right direction, specifically, in the upper-lower direction. The longitudinal ribs 230 are formed to cross a plurality of the lateral ribs 220.

The lateral ribs 220 extending in the left-right direction includes a first lateral rib 221, a second lateral rib 222, a third lateral rib 223, a fourth lateral rib 224, and a fifth lateral rib 225.

The first lateral rib 221 is a rib formed at an upper end portion of the center portion 211. The first lateral rib 221 is located at a position higher than a position of the uppermost plate-shaped part of the first side portion 212 located at the highest position in the upper-lower direction.

The second lateral rib 222 includes ribs formed across a rear-side surface of the left first side portion 212, a rear-side surface of the center portion 211, and a rear-side surface of the corresponding right first side portion 212. The second lateral rib 222 is formed for each of the five pairs of the plate-shaped parts of the first side portion 212. In other words, the second lateral rib 222 consists of five ribs corresponding to the five pairs of the plate-shaped parts of the first side portion 212.

The third lateral rib 223 and the fourth lateral rib 224 are ribs formed across a rear-side surface of the left second side portion 213, a rear-side surface of the center portion 211, and a rear-side surface of the right second side portion 213. The third lateral rib 223 is disposed at much the same position as that of the upper end portion of the second side portion 213 in the upper-lower direction. The fourth lateral rib 224 is disposed at much the same position as that of the center of the second side portion 213 in the upper-lower direction. The fourth lateral rib 224 includes a fourth lateral rib 224A disposed above and a fourth lateral rib 224 B disposed below.

The fifth lateral rib 225 is a rib formed at the lower end portion of the center portion 211. The fifth lateral rib 225 is disposed below the fourth lateral rib 224 (224B) in the upper-lower direction.

The plurality of longitudinal ribs 230 that extends in the upper-lower direction includes first longitudinal ribs 231, second longitudinal ribs 232, third longitudinal ribs 233, fourth longitudinal ribs 234, and fifth longitudinal ribs 235.

The first longitudinal ribs 231 are ribs formed at the left and right ends, respectively, on the back side of the center portion 211. An upper end of each first longitudinal rib 231 is connected to the first lateral rib 221, and a lower end of each first longitudinal rib 231 is connected to the fourth lateral rib 224B.

The second longitudinal ribs 232 are ribs formed inward of the respective first longitudinal ribs 231 in the left-right direction. Two second longitudinal ribs 232 are located apart from each other in the left-right direction. The upper ends of the second longitudinal ribs 232 extend to the upper end portion of the center portion 211, and the lower ends of the second longitudinal ribs 232 are connected to the fourth lateral rib 224B. Extended portions 251 of an attaching wire 250 which will be described below is located between the first longitudinal ribs 231 and the second longitudinal ribs 232 in the left-right direction. In other words, the extended portions 251 are disposed between the first longitudinal ribs 231 and the second longitudinal ribs 232 in the left-right direction.

The third longitudinal ribs 233 are ribs formed inward of the second longitudinal ribs 232 in the left-right direction at the upper part of the center portion 211. Four third longitudinal ribs 233 are formed side by side in the left-right direction. The upper ends of the third longitudinal ribs 233 extend to the upper end portion of the center portion 211, and the lower ends of the third longitudinal ribs 233 are connected to one of the five ribs included in the second lateral ribs 222 that is located next to the uppermost one.

The fourth longitudinal ribs 234 are ribs formed inward of the second longitudinal ribs 232 in the left-right direction at the lower part of the center portion 211. Two fourth longitudinal ribs 234 are formed side by side in the left-right direction. The fourth longitudinal ribs 234 have their upper ends connected to the third lateral rib 223 and extend with their lower ends positioned in the lower end portion of the center portion 211.

The fifth longitudinal ribs 235 are ribs formed at the left and right outer end portions of the rear-side surface of the left and right side portions 213. The upper ends of the fifth longitudinal ribs 235 are connected to the left and right outer ends of the third lateral rib 223. The left and right outer ends of the fourth lateral ribs 224 are also connected to the fifth longitudinal ribs 235.

As shown in FIG. 4, the pressure-receiving member body 210 (center portion 211) includes a first fixing area 214 and a second fixing area 215 to which a radio wave sensor 100, which will be described later, is fixed. The pressure-receiving member 200 has a plurality of (specifically, two) first fixing areas 214 and a plurality of (specifically, two) second fixing areas 215.

The first fixing area 214 is an area surrounded by the third lateral rib 223, the fourth lateral rib 224A, the second longitudinal rib 232, and the fourth longitudinal rib 234. The first fixing area 214 is disposed on or around the upward end portion of the second side portion 213 in the upper-lower direction. The left and right first fixing areas 214 are provided to the left and to the right, respectively, in the center of the pressure-receiving member 200. The first fixing areas 214 are disposed between a pair of the left and right extended portions 251 of the attaching wire 250 in the left-right direction.

Hereafter, in the present embodiment, the third lateral rib 223 and the fourth lateral rib 224A correspond to "a plurality of first ribs," the second longitudinal ribs 232 and the fourth longitudinal ribs 234 correspond to "a plurality of second ribs," and the first fixing area(s) 214 correspond to "a surrounded area(s)."

The second fixing area 215 is an area defined inside an approximately U-shaped portion by the fourth lateral rib 224B, the fifth lateral rib 225, and each of the fourth longitudinal ribs 234. The second fixing area 215 is disposed on or around a lower end portion of the second side portion 213 in the upper-lower direction. The two left and right second fixing areas 215 are provided to the left and to the right, respectively, in the center of the pressure-receiving member 200. Each second fixing area 215 is disposed below the corresponding first fixing area 214 located in a corresponding position in the left-right direction. Specifically, the left second fixing area 215 is disposed below the left first fixing area 214, and the right second fixing area 215 is disposed below the right first fixing area 214.

A through hole 216 for a screw 190 to be screwed in (refer to FIG. 5) is provided at each of the first fixing areas 214 and the second fixing areas 215.

Referring back to FIG. 3, the attaching wire 250 is a metal wire member bended in an approximately U-shaped configuration that includes a pair of left and right extended portions 251 that extend in an upper-lower direction, a pair of left and right upper attaching portions 252 that extend upward from the respective extended portions 251, and a lower attaching portion 253 that connects the lower parts of the pair of left and right extended portions 251. The pair of left and right extended portions 251 are parts that support the pressure-receiving member 200. The attaching wire 250 is formed integrally with the pressure-receiving member 200 by insert molding the pair of left and right extended portions 251 to the pressure-receiving member 200. A plurality of attaching clips 260 are attached to the lower attaching portions 253.

The pressure-receiving member 200 is attached to the seatback frame F2 by inserting the upper attaching portions 252 of the attaching wire 250 into through holes (not shown in the figures) formed in the bridging frame 15, and engaging the attaching clips 260 to through holes (not shown in the figures) formed in the lower frame 16. The pressure-receiving member 200 is configured to be able to move rearward when a load from the occupant is received. In the car seat S, the impact to the neck of the occupant may be reduced by the pressure receiving member 200 moving rearward upon receiving a rearward load exceeding a predetermined amount, such as in situations where a car in which the car seat S is installed is rear-ended by another car, or when a rear end of the car with the car seat S installed collides with other cars or structures while backing up, etc.

As shown in FIG. 3 and FIG. 4, the vehicle seat S further includes a radio wave sensor 100. The radio wave sensor 100 is a sensor that acquires information about an occupant seated on the vehicle seat S, by emitting radio waves toward the occupant and detecting the radio waves reflected off the occupant. The information about the occupant includes, for example, heartbeats, pulse rate, amplitude of a pulse, respiration rate, and depth of respiration. In other words, the radio wave sensor 100 detects at least one of the heartbeats or the respiration of the occupant.

As shown in FIG. 5, the radio wave sensor 100 includes a sensor part 110 that acquires information about the occupant, a case 120 that holds the sensor part 110, and a plurality of fixing parts 130.

The sensor part 110 include an emitting part 111 that emits radio waves toward the occupant, and a detecting part 112 for detecting radio waves reflected by the surface of the skin of the occupant. The sensor part 110 of the radio wave sensor 100 may be, for example, a microwave Doppler sensor.

The radio wave sensor 100 is provided in the seatback S2, similarly to the pressure-receiving member 200. To be more specific, the radio wave sensor 100 is fixed to the pressure-receiving member 200. The fixing part 130 is a part that is fixed to the pressure-receiving member 200.

As shown in FIG. 4, four fixing parts 130 are provided, one at each of the four corners of the front side surface of the case 120. Each fixing part 130 includes an approximately cylindrically-shaped fixing body 130A protruding from the case 120, and a plurality of reinforcing ribs 130B protruding from an outer peripheral surface of the fixing body 130A. Four reinforcing ribs 130B are provided, evenly spaced apart from each other on the outer peripheral surface of the fixing body 130A. The rear ends of the reinforcing ribs 130B are connected to the case 120.

The fixing parts 130 include a first fixing part 131 and a second fixing part 132. The radio wave sensor 100 includes a plurality of first fixing parts 131 and a plurality of second fixing parts 132. To be more specific, the radio wave sensor 100 includes two first fixing parts 131 and two second fixing parts 132.

The first fixing part 131 is a fixing part that is fixed to each first fixing area 214 of the backside surface 210B of the pressure-receiving member body 210. The first fixing parts 131 are provided at the upper end of the front side of the case 120, spaced apart to the left and to the right. Each first fixing part 131 is fixed to a different first fixing area 214. To be more specific, one of the first fixing parts 131 is fixed to the left first fixing area 214, and the other first fixing part 131 is fixed to the right first fixing area 214.

The second fixing part 132 is a fixing part that is fixed to each second fixing area 215 of the backside surface 210B of the pressure-receiving member body 210. The second fixing parts 132 are provided at the lower end of the front side of the case 120, spaced apart to the left and to the right. Each second fixing part 132 is located below the corresponding first fixing part 131 located in a corresponding position in the left-right direction. To be more specific, one of the second fixing parts 132 is disposed below the left first fixing part 131 and the other second fixing part 132 is disposed below the right first fixing part 131. Each second fixing part 132 is fixed to a different second fixing area 215. To be more specific, one of the second fixing parts 132 is fixed to the left second fixing area 215, and the other of the second fixing parts 132 is fixed to the right second fixing area 215.

As shown in FIG. 5, each fixing part 130 is fixed to the pressure-receiving member 200 by a screw 190. To be more specific, the radio wave sensor 100 is disposed at the rear side of the center portion 211 of the pressure-receiving member body 210, and is fixed to the backside 210B of the pressure-receiving member 200 by screws 190 applied from the front side via through holes 216 of the pressure-receiving member 200 and fastened to the fixing part body 130A of the fixing part 130. The inner surface of the fixing part body 130A may or may not form a screw groove.

As shown in FIG. 3, the radio wave sensor 100 is disposed at the lower part of the pressure-receiving member 200. Specifically, the radio wave sensor 100 is disposed at the lower part of the center portion 211. To be more specific, the radio wave sensor 100 is located between the left and right second side portions 213 in the upper-lower direction. The lower part of the pressure receiving member 200 is a part of the pressure receiving member 200 that deforms the least upon receipt of pressure exceeding a predetermined pressure from the occupant.

According to the embodiment described above, the following advantageous effects may be achieved.

As shown in FIG. 4, the first surrounded area 214 of the pressure-receiving member 200 is surrounded by the ribs 223, 224A, 232, and 234, and is thus configured as a part having an increased rigidity that does not easily deform; therefore the attachment rigidity of the radio wave sensor 100, that is, the structural rigidity or firmness provided in the first fixing area and the radio wave sensor 100 fixed thereto may be increased.

Since the radio wave sensor 100 have a plurality of the first fixing parts 131, the attachment rigidity of the radio wave sensor 100 may be increased more because a plurality of parts of the radio wave sensor 100 are fixed to the first fixing areas 214 of the pressure-receiving member 200.

Since the pressure-receiving member 200 have a plurality of the first fixing areas 214, each of the first fixing areas 214 may be made smaller compared to when a plurality of parts of the radio wave sensor 100 is fixed to one surrounded area; therefore, the rigidity of the first fixing areas 214 are increased. In consequence, by fixing each of the first fixing areas 131 to the corresponding first fixing area 214 with high rigidity, the attachment rigidity of the radio wave sensor 100 is increased furthermore.

Since the first fixing area 214 is located at each of the left and right side of the center of the pressure-receiving member 200 in the left-right direction, the radio wave sensor 100 may be disposed to cross the center. This prevents the weight of the pressure-receiving member 200 from being imbalanced.

Since the radio wave sensor 100 is located at the lower part of the pressure-receiving member 200, in other words, the radio wave sensor 100 is not attached to the upper part of the pressure-receiving member 200, a sufficient amount of flexibility of the upper part of the pressure-receiving member may be ensured.

Since the first fixing areas 214 are provided between the pair of left and right extended portions 251 of the attaching wire 250, the attaching wire 250 supports both the left side and the right side of the first fixing areas 214, and the attachment rigidity of the radio wave sensor 100 may be increased more.

Since the fixing parts 130 are fixed to the pressure-receiving member 200 by the screws 190, the radio wave sensor 100 may be attached to the pressure-receiving member 200 relatively easily.

Although the first embodiment has been described above, the vehicle seat proposed in this disclosure is not limited to the above-described embodiment, and may be modified where appropriate as in the examples shown below.

For example, the radio wave sensor 100 is disposed at the lower part of the pressure-receiving member 200 in the above embodiment, but the position of the radio wave sensor is not limited to this configuration, and the radio wave sensor 100 may be disposed at any positions other than the lower part of the pressure-receiving member.

In the above-described embodiment, the pressure-receiving member 200 includes a plurality of first fixing areas 214 (surrounded area), and each of the first fixing parts 131 is fixed to a different first fixing area 214, but the surrounded area is not limited to this configuration. For example, a plurality of first fixing parts may be fixed to one and the same surrounded area, and in this instance, the pressure-receiving member may be configured to include only one surrounded area.

In the above-described embodiment, the radio wave sensor 100 includes four fixing parts 130, but the number of fixing parts is optional. That is, the radio wave sensor may be configured to have at least one fixing part, and the number of the fixing part is not limited to four, and may be less than three or more than five. The number of the first fixing parts fixed to the surrounded area(s) of the pressure-receiving member is also optional. For example, all of the fixing parts may be configured to be first fixing parts, or the fixing parts may be configured such that only one of a plurality of fixing parts may be a first fixing part of a radio wave sensor. There may be two or more surrounded area provided at each of the left and right sides of the center of the pressure-receiving member in the lateral direction depending on the number of the first fixing parts.

The above-described embodiment is configured such that the radio wave sensor 100 is fixed to the center portion 211 of the pressure-receiving member 200, but the arrangement of the radio wave sensor 100 is not limited to this embodiment. Instead, the radio wave sensor 100 may be fixed to any of the first side portions 212 or the second side portions 213 of the pressure-receiving member 200, for example. In cases where the radio wave sensor 100 is fixed to the first side portions 212, the radio wave sensor 100 may be arranged to extend across a plurality of the first side portions 212 lined up in the upper-lower direction. In cases where the radio wave sensor 100 is fixed to the first side portions 212, the radio wave sensor 100 may be fixed to one first side portion 212, or the radio wave sensor 100 may be fixed to a plurality of first side portions 212. By adopting the configuration in which the radio wave sensor 100 is fixed to the side portion, the radio wave sensor may be firmly fixed to the pressure-receiving member in such an alternative embodiment as will be described later (see second embodiment) in which the pressure-receiving member is supported from the rear side by a support member that deforms the shape of the pressure member.

The above-described embodiment is configured such that the fixing part 130 is fixed to the pressure-receiving member 200 by the screws 190, but the arrangement of the fixing part is not limited to this embodiment. For example, the fixing part may be a clip like the fixing clip 260 in the above-described embodiment, and may be engaged to a through hole formed on the pressure receiving member and thereby fixed to the pressure-receiving member.

The specific configuration of the pressure-receiving member is not limited to the configuration in the above-described embodiment. For example, the lateral ribs 223, 224A (first ribs) and the longitudinal ribs 232, 234 (second ribs) cross perpendicularly in the above-described embodiment, but the first ribs and the second ribs merely needs to cross each other, and do not have to cross perpendicularly. The location and the number of the ribs are also optional. In the above-described-embodiment, the pressure-receiving member 200 is configured to include the center portion 211 and side portions 211 and 212, but the pressure-receiving member may be configured to not include side portions, for example. In the above-described embodiment, the pressure-receiving member 200 is formed integrally with the attaching wire 250, but the pressure-receiving member and the attaching wire may be formed separately, and the attaching wire may be configured to be attached to the pressure-receiving member when the pressure-receiving member is attached to the seatback frame.

In the above-described embodiment, the pressure-receiving member 200 and the radio wave sensor 100 are provided in the seatback S2, but the pressure-receiving member and the radio wave sensor may be provided in the seat cushion S1. When the pressure-receiving member and the radio wave sensor are provided in the seat cushion, the upper side corresponds to "the side facing the occupant, or an occupant side," and the lower side corresponds to "the side facing away from the occupant, or a side facing way from the occupant." A pressure-receiving member and a radio wave sensor may also be provided in both the seat cushion S1 and the seatback S2.

Next, a detailed description of a second embodiment will be given with reference made mainly to FIG. 6 to FIG. 11 where appropriate. Hereafter, elements having substantially the same configurations as those of the first embodiment will be designated by the same reference characters, and descriptions thereof will be omitted, and elements that are different from those of the first embodiment will be described in detail. The car seat S according to the second embodiment as an example of a vehicle seat is mainly different from the car seat described in the first embodiment in that the car seats include a lumbar support device that supports the pressure-receiving member from the side away from the occupant side and deforms the shape of the pressure-receiving member.

As shown in FIG. 6, a seat frame F includes a seat cushion frame F1 and a seatback frame F2, and the seatback frame F2 is connected to the rear end portion of the seat cushion frame F2 via a reclining mechanism, similarly to the first embodiment.

The seat cushion frame F1 includes a pair of side frames 21 disposed separately in the left-right direction, a pan frame 22 that connects front portions of the side frames 21, and a rear frame 24 that connects rear portions of the side frames 21.

The side frames 21 and the pan frame 22 are sheet metal members, and the rear frame 24 is a pipe member.

The seat cushion frame F1 supports a mat member 25 that receives a load from an occupant seated on the car seat S. The mat member 25 includes a plurality of metal wires that extends in the front-rear direction while bending to the left and right alternately and a plurality of plastic members formed integrally with the metal wires, and is arranged to bridge the pan frame 22 and the rear frame 24.

As shown in FIG. 7, the seatback frame F2 includes, a pair of sheet metal frames 12 disposed separately from each other to the left and to the right, and a pipe frame 13 made by bending a pipe member in a U-shape and connected to the upper ends of the pair of sheet metal frames 12.

The pipe frame 13 includes a pair of left and right upper side frames 13A that extend straight from the sheet metal frames 12 upward to some midpoint and slightly inclined therefrom toward laterally inner sides of the sheet metal frames 12. The left and right sheet metal frames 12 and upper side frames 13A are a pair of side frames 11 disposed separately to the left and to the right. The pipe frame 13 includes an upper frame 13B that connects the upper ends of the pair of upper side frames 13A, in other words, the upper end portions of the side frame 11.

The seatback frame F2 also includes, a lower frame 14 which connects the lower parts of the side frames 11, specifically, the lower parts of the sheet metal frames 12, and a bridging frame 15 that connects the upper parts of the side frames 11, specifically, the left and right upper side frames 13A at a position lower than that of the upper frame 13B.

The lower frame 14 is a sheet metal member in which the upper edge and the lower edge extend toward the front as viewed in cross section. The lower frame 14 has an elongated shape long in the lateral direction with the left and right ends welded to portions of the left and right sheet frames 12 that extend laterally inwards. Two attaching holes 14A are formed separately to the left and to the right at the center portion of the lower frame 14, i.e. the lower part of the seatback frame F2. In a normal posture in which the seatback frame F2 is not reclined, the lower frame 14 faces forward and rearward, wherein each attaching hole 14A is a through hole that extends in the front-rear direction. The attaching hole 14A is a part in which a screw for fixing a lower latch part 60 of a lumbar support device LS which will be described later (an element that corresponds to a screw 91 represented in FIG. 12 showing a third embodiment which will be described later) is to be inserted.

The bridging frame 15 includes a lower flange 15A that extends forward from the lower edge of the bridging frame 15. Support holes 15B that extend through the lower flange 15A are formed on the lower flange 15A. One support hole 15B is formed at each of the left and right end portions of the lower flange 15A.

The seatback frame F2 supports a lumbar support device LS. The lumbar support device LS receives the force of the occupant leaning back on the seatback S2 and conveys the force to the seatback frame F2, and deforms a part that contacts the lumbar region of the occupant to change the support state of the lumbar region to a state favorable to the occupant.

The lumbar support device LS includes a pressure-receiving member 40 which receives the load from the occupant via the seatback pad P2 (refer to FIG. 1), a support member 50 that supports the pressure-receiving member 40 from the rear side (backside), and causes the pressure-receiving member 40 to change shape, and a lower latch part 60 that fixes the lower part of the support member 50 (the lumbar support device LS) to the lower frame 14.

The pressure-receiving member 40 is a plate-shaped member made of plastic or the like, and includes a center portion 41 located at the center of the pressure-receiving member 40 in the left-right direction, and a pair of left and right side portions 42 that are disposed at the left and right sides of the center portion and project forward of the center portion 41.

The center portion 41 is located directly behind of the occupant's back. The center portion 41 is pushed by an arch member 58 (which will be described later) of the support member 50.

The side portions 42 are disposed in such position that the left and right sides of the occupant's back are supported thereby. Each side portion 42 has a plurality of narrow plate-shaped parts that extends outward in the lateral direction, such that the sides of the occupant's back may be flexibly supported by the narrow plate-shaped part. The four narrow plate-shaped parts located below have their front ends connected, and are a little more rigid than the five other plate-shaped parts located above.

Two attaching hooks 43 are disposed at the rear-side surface of the pressure-receiving member 40. Each attaching hook 43 has a shape of a letter C that opens rearward.

The support member 50 includes a guide wire 51, an upper connecting part 52, a lower connecting part 53, a lower ascent/descent plate 54 as an example of a first plate-shaped member, an upper ascent/descent plate 55 as an example of a second plate-shaped member, a support part ascent/descent mechanism 56 (refer to FIG. 8), an arch deforming mechanism 57 (refer to FIG. 8), arch members 58 that are flexibly deformable, and a support wire 59.

The guide wire 51 is a wire that extends in an upper-lower direction, and has two guide wire portions parallel to each other and separated apart from each other in the left-right direction. Though not shown in the figures, the two guide wire portions of the guide wire 51 are connected inside the lower connecting part 53 to form a single U-shaped wire.

The upper connecting part 52 is a part that connects upper parts of the two guide wire portions of the guide wire 51. The upper connecting part 52 is a plastic member formed integrally with the guide wire 51 by insert molding. Two cylindrical support protrusions 52A which have an axis in the left-right direction are disposed to the left and to the right on the front surface of the upper connecting part 52. The support protrusions 52A are disposed at positions that correspond to the two attaching hooks 43, engaged to the attaching hooks 43 and thereby pivotally support the pressure-receiving member 40.

The lower connecting part 53 connects the lower parts of the two guide wire portions of the guide wire 51, keeps the rigidity of the lower portion of the guide wires 51, and fixes the lumbar support device LS to the seatback frame F2. The lower connecting part 53 is a plastic member formed integrally with the guide wires 51 by insert molding, and, as described above, the lower part of the U-shaped guide wire 51 is held inside.

As shown in FIG. 8, two protrusions 53A are provided separately to the left and to the right at the lower part of the rear-side surface of the lower connecting part 53. The protrusions 53A are parts that come in contact with the front surface of the lower frame 14 when the lumbar support device LS is attached to the seatback frame F2. Fixing holes 53B are formed to the left and to the right at the rear-side surface of the lower connecting part 53. Each fixing hole 53B is a hole for a screw (refer to a screw 91 in FIG. 12) to be screwed in, and may have a thread formed thereon, or may not have a thread thereon.

Further, a restricting part 53C projecting rearward from the rear-side surface of the lower connecting part 53 is provided at the center in the left-right direction. The restricting part 53C engages with the top of the lower frame 14 and restricts the position of the lumbar support device LS in the upper-lower direction. A latching part 53D that extends in the downward direction is formed at the rear end portion of the restriction part 53C, and the lumbar support device LS is made unlikely to come off by the latching part 53D when the latching part 53D is hooked to the lower frame 14.

The lower ascent/descent plate 54 is movable in upward and downward directions. Specifically, the lower ascent/descent plate 54 moves in upward and downward directions while being guided by the guide wire 51. The lower ascent/descent plate 54 has guide parts 54A at the left and right ends and each guide part 54A has a groove that is engageable with a corresponding guide wire portion of the guide wire 51 so that the guide parts 54A engage with the guide wire 51. A stepper motor 56B of the support part ascent/descent mechanism 56 and a stepper motor 57B of the arch deforming mechanism 57 are fixed to the back surface of the lower ascent/descent plate 54.

The upper ascent/descent plate 55 is a member that may move toward or away from the lower ascent/descent plate 54 in upward and downward directions. Specifically, the upper ascent/descent plate 55 is located above the lower ascent/descent plate 54 and moves in upward and downward directions while being guided by the guide wire 51. The upper ascent/descent plate 55 has guide parts 55A at the left and right ends and each guide part 55A has a groove that is engageable with a corresponding guide wire portion of the guide wires 51 so that the guide parts 55A engage with the guide wire 51.

The support part ascent/descent mechanism 56 is a mechanism for moving the lower ascent/descent plate 54 and the upper ascent/descent plate 55 together upward and downward, and includes a threaded shaft 56A, a stepper motor 56B, a nut 56C, an upper end fixing part 56D, and a lower end fixing part 56E.

The threaded shaft 56A is a bar with an external screw thread formed around the bar, and extends in the upper-lower direction.

The stepper motor 56B is an electric motor rotatable in the forward and reverse directions, with an output shaft that is caused to rotate by a controller (not shown in the figures).

The nut 56C is connected to the stepper motor 56B by a gear mechanism (not shown in the figures) and is rotatable in the forward and reverse directions corresponding to the directions of the rotation of the stepping motor 56B. The nut 56C is engaged with the threaded shaft 56A, and may move upward and downward relative to the threaded shaft 56A by rotating.

The upper fixing part 56D is provided at the upper end of the threaded shaft 56A and fixes the upper end of the threaded shaft 56A to the rear surface of the upper connecting part 52.

The lower fixing part 56E is provided at the lower end of the threaded shaft 56A and fixes the lower end of the threaded shaft 56A to the rear surface of the lower connecting part 53.

The arch deforming mechanism 57 is a mechanism for moving the upper ascent/descent plate 55 upward and downward relative to the lower ascent/descent plate 54, and includes a threaded shaft 57A, a stepper motor 57B, a nut 57C, an upper fixing part 57D, and a cap 57E.

The threaded shaft 57A is a bar with an external screw thread formed around the bar and extends in the upper-lower direction.

The stepper motor 57B is an electric motor rotatable in the forward and reverse directions, with an output shaft that is caused to rotate by a controller (not shown in the figures).

The nut 57C is connected to the stepper motor 57B by a gear mechanism (not shown in the figures), and is rotatable in the forward and reverse directions corresponding to the directions of the rotation of the stepping motor 57B. The nut 57C is engaged with the threaded shaft 57A, and may move upward and downward relative to the threaded shaft 57A by rotating.

The upper fixing part 57D is provided at the upper end of the threaded shaft 57A and fixes the upper end of the threaded shaft 57A to the rear surface of the upper ascent/descent plate 55.

The cap 57E is provided at the lower end of the threaded shaft 57A and restrains the lower end of the threaded shaft 57A from catching on objects around the threaded shaft 57A.

Referring back to FIG. 7, each of the arch members 58 is a belt-shaped member that extends long in the upper-lower direction, and is formed from an elastic metal plate or the like. The lower end (one end) of the arch members 58 is fixed to the front surface of the lower ascent/descent plate 54 by a screw, rivet, etc., and the upper end (the other end) is fixed to the front surface of the upper ascent/descent plate 55 by a screw, rivet, etc. Two arch members 58 are provided side by side to the left and to the right near each of the left and right ends of the lower ascent/descent plate 54 and the upper ascent/descent plate 55, and are placed to face the rear surface of the center portion 41 of the pressure-receiving member 40.

As shown in FIG. 8, the support wire 59 is a wire with a circular cross sectional shape and is disposed to have its two end portions extending upward from the left and right ends of the upper connecting part 52. The support wire 59 is formed integrally with the upper connecting part 52 by insert molding. Though not shown in the figures, the lower ends of the two upwardly extending end portions of the support wire 59 are connected, so that the support wire 59 forms a single U-shaped wire.

The two upwardly extending portions of the support wire 59 are inserted into the support holes 15B of the bridging frame 15 (refer to FIG. 6). This restricts the position of the upper part of the lumbar support device LS in the front-rear direction and the left-right direction. Covered parts 59A covered by a resin having good sliding properties such as nylon are provided at the upper end portions of the support wire 59, specifically the segments that are contactable with the support holes 15B. Provision of the covered part 59A restrains noise from occurring when the support wire 59 is caused to slide upward and downward relative to the support holes 15B by the occupant applying a load to the seatback S2 or lifting the load from the seatback S2.

Here, operation of the lumbar support device LS will be described briefly.

When the nut 56C is caused to turn by rotation of the output shaft of the stepper motor 56B, the nut 56C moves relative to the threaded shaft 56A, as shown in FIG. 9A. For example, when the nut 56C moves upward relative to the threaded shaft 56A, as shown in FIG. 9A, the upper ascent/descent plate 55 and the lower ascent/descent plate 54 moves upward together. The upper ascent/descent plate 55 and the lower ascent/descent plate 54 are guided by the guide wire 51 and slide along the guiding wire 51.

When the nut 57C is caused to turn by rotation of the output shaft of the stepper motor 57B, the nut 57C moves relative to the threaded shaft 57A, as shown in FIG. 9B. Since the nut 57C cannot move upward or downward relative to the lower ascent/descent plate 54, the threaded shaft 57A moves upward or downward when the nut 57C turns. For example, when the nut 57C turns, the threaded shaft 57A moves downward, and causes the upper ascent/descent plate 55 to move downward relative to the lower ascent/descent plate 54, as shown in FIG. 9B. The upper ascent/descent plate 55 and the lower ascent/descent plate 54 slide along the guiding wire 51.

When the upper ascent/descent plate 55 moves toward the lower ascent/descent plate 54, as in FIG. 9B, a surplus of the length of the arch member 58 is produced over the length between the upper ascent/descent plate 55 and the lower ascent/descent plate 54, and the arch member 58 bends and juts out into an arcuate shape, as shown in FIG. 10. The front surface of the arch member 58 pushes the rear surface of the center portion 41 of the pressure-receiving member 40, and causes the center portion 41 to deform into an arcuate shape jutting frontward.

By the forward and reverse rotation of the stepper motor 57B, the amount of protrusion of the pressure-receiving member 40 in the forward direction may be controlled, and by the forward and reverse rotation of the stepper motor 56B, the position of the protrusion of the pressure-receiving member 40 in the upper-lower direction may be controlled. This makes it possible to support the occupant's lumbar suitably.

As shown in FIG. 8 and FIG. 11, the vehicle seat further includes a radio wave sensor 100. As shown in FIG. 11, the radio wave sensor 100 includes a sensor part 110 for acquiring the information about the occupant and a case 120 for holding the sensor part 110. The sensor part 110 includes an emitting part 111 that emits radio waves toward the occupant, and a detecting part 112 that detects the radio waves that are reflected by the surface of the skin of the occupant. The radio wave sensor 100 may be, for example, a microwave Doppler sensor.

The radio wave sensor 100 is provided on the seatback S2, similarly to the pressure-receiving member 40 and the support member 50. In the second embodiment, the radio wave sensor 100 is attached to the pressure-receiving member 40. Specifically, the radio wave sensor 100 is attached to one of the side portions 42 of the pressure-receiving member 40.

The side portions 42 extend from each of the left and right ends of the center portion 41 in a diagonally forward and laterally outward direction so that the side portions extend forward as the side portions extend laterally outward. As shown in FIG. 7 and FIG. 8, each side portion 42 includes five upper first side parts 42A each having a narrow plate-shaped part, and a second side part 42B having four narrow plate-shaped parts, the outer ends of which are connected; the second side part 42B is disposed below the first side parts 42A.

Specifically, each first side part 42A has a plate shape of which the width in the upper-lower direction is shorter than the length in the left-right direction. The second side part 42B includes a plurality of plate-shaped parts 42C, each of which the width in the upper-lower direction is shorter than the length in the left-right direction, specifically, four plate-shaped parts 42C spaced apart from each other in the upper-lower direction, and a connecting part 42D extending in the upper-lower direction and connecting the outer ends of the four plate-shaped parts 42C. The second side part 42B is located at the lower part of the pressure-receiving member 40.

The radio wave sensor 100 is attached to the right second side part 42B of one of the two side portions 42. To be more specific, the radio wave sensor 100 is fixed to the rear-side surface of the right second side part 42B. Specifically, the radio wave sensor 100 is disposed at the back side of the second side part 42B and a plurality of screws 92 (refer to FIG. 11) fixes the case 120 to the second side part 42B, so that the radio wave sensor 100 is attached to the rear-side surface of the second side part 42B.

The radio wave sensor 100 is attached to the second side part 42B disposed at the lower part of the pressure-receiving member 40 and thereby disposed at the lower part of the pressure-receiving member 40, as shown in FIG. 8. The radio wave sensor 100 is arranged across a plurality of plate-shaped parts 42C in the upper-lower direction. Specifically, the radio wave sensor 100 is arranged across the upper two plate-shaped parts 42C in the upper-lower direction.

The radio wave sensor 100 is arranged at such a position as not to overlap the support member 50 when seen from the rear side. In other words, the radio wave sensor 100 is disposed at a position different from the position of the support member 50 when seen from the rear side. To be more specific, the radio wave sensor 100 is located at a position shifted in the left-right direction, specifically to the right of the support member 50. The radio wave sensor 100 is located at such a position that the arch member 58 of the support member 50 does not press the radio wave sensor 100.

From the above-described second embodiment, by attaching the radio wave sensor 100 to the side portion 42 of the pressure-receiving member 40, the radio wave sensor 100 may be placed in such a position as not to interfere with the movement of the support member 50 or the pressure-receiving member 40.

Since the radio wave sensor 100 is attached to the rear-side surface of the side portion 42, the discomfort the occupant seated on the vehicle seat would otherwise feel from the radio wave sensor 100 via the seatback pad P2 may be suppressed.

Since the side portion 42 extends diagonally forward and laterally outward from each of the left and right ends of the center portion 41, it is easier to arrange the radio wave sensor 100 so as to be oriented toward the occupant. By arranging the radio wave sensor 100 so as to be oriented toward the occupant, the detection accuracy of the radio wave sensor 100 may be increased.

Since each first side part 42A is a narrow plate shape, the amount of flexibility of the side portion 42 of the pressure-receiving member 40 may be ensured by the first side part 42A. Since the second side part 42B is shaped by connecting the ends of a plurality of narrow plate-shaped parts 42C, the rigidity of the second side part 42B to which the radio wave sensor 100 is attached may be increased, so that the attaching rigidity of the radio wave sensor 100 may be increased. Therefore, ensuring the amount of flexibility of the side portion 42 of the pressure-receiving member 40 and increasing the attaching rigidity of the radio wave sensor 100 are compatible.

Since the second side part 42B is disposed at the lower part of the pressure-receiving member 40, the discomfort the occupant may feel from the second side part 42B to which the radio wave sensor 100 is attached, as would be caused when the support member and the pressure-receiving member moves, may be suppressed.

Since the radio wave sensor 100 is arranged across a plurality of plate-shaped parts 42C of the side portion 42 (second side part 42B), the radio wave may be emitted through between the plate-shaped parts 42C, and the reflected waves of the radio waves may be detected through between the plate-shaped parts 42C. This enables the radio wave sensor 100 to emit and detect the radio waves without fail.

The radio wave sensor 100 may be attached to the left second side part 42B instead of the right second side part 42B as shown in FIG. 8 by a chain double dashed line.

The radio wave sensor 100 may be attached to the first side parts 42A instead of the second side part 42B. If the radio wave sensor 100 is attached to the first side parts 42A, the radio wave sensor 100 may be arranged across a plurality of the first side parts 42A in the upper-lower direction. In this instance, the plurality of first side parts 42A corresponds to the "plurality of plate-shaped parts."

If the radio wave sensor 100 is so small that an occupant is unlikely to feel the sensor, the radio wave sensor 100 may be attached to the front-side surface of the side portion 42 instead of the rear-side surface of the side portion 42.

Next, a third embodiment will be described in detail. Hereafter, for elements having substantially the same configurations as those of the embodiments described above will be designated by the same reference characters, and a description thereof will be omitted, and elements that are different from the above-described embodiments will be described in detail.

As shown in FIG. 12, the radio wave sensor 100 is attached to the support member 50 in the third embodiment. Specifically, the radio wave sensor 100 is attached to the lower ascent/descent plate 54. To be more specific, the radio wave sensor 100 is attached to the rear-side surface of the lower ascent/descent plate 54. To be more specific, the radio wave sensor 100 is disposed at the rear-side surface of the lower ascent/descent plate 54, and is attached to the rear-side surface of the lower ascent/descent plate 54 by fixing the case 120 to the lower ascent/descent plate 54 by a plurality of screws (not shown in the figures).

The radio wave sensor 100 is disposed at such a position as not to overlap the threaded shafts 56A and 57A, and the stepper motors 56B and 57B. Specifically, the radio wave sensor 100 is disposed at a position that is shifted from the threaded shaft 56A and 57A in the left-right direction and shifted from the stepper motor 56B and 57B in the upper-lower direction. In the third embodiment, the radio wave sensor 100 is disposed at a position that is to the right of the threaded shaft 56A and above the stepper motor 57B. The radio wave sensor 100 is disposed at a position that is not between the pressure-receiving member 40 and the support member 50, and a position that is not between the lower ascent/descent plate 54 and the upper ascent/descent plate 55.

As shown in FIG. 13A, the vehicle seat S of the third embodiment further includes a sensor orientation changing mechanism 70. The sensor orientation changing mechanism 70 is a mechanism for changing the orientation of the radio wave sensor 100 according to the position of the radio wave sensor 100 in the upper-lower direction, and includes a controller 71 and an actuator 72.

The actuator 72, for example, includes a stepper motor (not shown in the figures) and a swinging shaft 72C.

The stepper motor is an electric motor which has an output shaft rotated by the controller 71 in a forward and reverse direction.

A gear mechanism includes a plurality of gears, and reduces the speed with which the driving power of the stepper motor is transmitted and transmits the driving power to the swinging shaft 72 C.

The swinging shaft 72C is disposed parallel to the lateral direction. As shown in FIG. 13B and FIG. 13C, the sensor part 110 of the radio wave sensor 100 is fixed to the swinging shaft 72C and supported so that the sensor part 110 swings upward and downward according to the case 120.

The controller 71 activates the actuator 72 to control the orientation of the sensor part 110 of the radio wave sensor 100. Specifically, the controller 71 detects the position of the radio wave sensor 100 in the upper-lower direction and drives the actuator 72 to control the orientation of the sensor part 110. The controller 71 detects the position of the radio wave sensor 100 by making use of the historical data of the operation of the stepper motor 56B that drives the threaded shaft 56A of the support part ascent/descent mechanism 56.

An example of the operation of the sensor orientation changing mechanism 70 will be described below.

As shown in FIG. 13B, the controller 71 causes the sensor part 110 of the radio wave sensor 100 to orient toward the occupant's back when the lower ascent/descent plate 54 descends. Specifically, the controller 71 drives the actuator 72 to rotate the swinging shaft 72C in the counterclockwise direction in the figure to cause the direction of the sensor part 110 to become oriented in a diagonally forward and upward direction when the lower ascent/descent plate 54 descends and the radio wave sensor 100 moves downward.

As shown in FIG. 13C, the controller 71 causes the radio wave sensor 100 to become oriented toward the occupant's back when the lower ascent/descent plate 54 ascends. Specifically, the controller 71 drives the actuator 72 to rotate the swinging shaft 72C in the clockwise direction in the figure to cause the sensor part 110 to become oriented forward when the lower ascent/descent plate 54 ascends and the radio wave sensor moves upward.

By the controller 71 driving the actuator 72 as described above, the orientation of the radio wave sensor (sensor part 110) may be changed according to the position of the radio wave sensor 100 in the upper-lower direction so that the radio wave sensor 100 becomes oriented toward the back of the occupant. This enables the radio wave sensor 100 to suitably acquire information about the occupant.

According to the above-described third embodiment, in which the radio wave sensor 100 is attached to the rear-side surface of the lower ascent/descent plate 54, the radio wave sensor 100 may be placed in such a position as not to interfere with the movement of the support member 50 or the pressure-receiving member 40 when the radio wave sensor 100 is mounted in the seatback S2.

Since the radio wave sensor 100 includes the sensor orientation changing mechanism 70, the radio wave sensor 100 may be oriented in an appropriate direction regardless of the position of the radio wave sensor 100 in the upper-lower direction, and the detection accuracy of the radio wave sensor 100 may be increased.

As shown in FIG. 14, the radio wave sensor 100 may be attached to the upper ascent/descent plate 54 instead of the lower ascent/descent plate 55. Specifically, the radio wave sensor 100 may be attached to the rear-side surface of the upper ascent/descent plate 55. This also enables the radio wave sensor 100 to be placed in such a position as not to interfere with the movement of the support member 50 or the pressure-receiving member 40.

For example, if the effect of change in the position of the radio wave sensor 100 in the upper-lower direction on the detecting accuracy of the radio wave sensor 100 is small, the sensor orientation changing mechanism may not be included.

The second embodiment and the third embodiment as described above may be put in to practice with appropriate changes made as in examples given below.

For example, the side portion 42 of the pressure-receiving member 40 may not be configured to include a plurality of narrow plate-shaped parts as shown in the second embodiment and the third embodiment. For example, the ends of all of the narrow plate-shaped parts may be connected to each other to form the side portions. Also, all of the narrow plate-shaped parts may be connected to each other, instead of just the ends being connected, to form the side portions. The side portion may also be in a form in which the side portion only extends from a part of the left and right ends of the center portion, for example, the side portions may be configured to only extend laterally outward from the upper part of the left and right ends of the center portion. The side portions may also only extend outward in the lateral direction instead of extending diagonally in the forward and laterally outward direction. When the radio wave sensor is attached to the support member, the pressure-receiving member may be formed without a side portion.

The pressure-receiving member 40, the support member 50, and the radio wave sensor 100 are provided in the seatback S2 in the second embodiment and third embodiment, but the pressure-receiving member, the support member, and the radio wave sensor may be provided in the seat cushion S1. For example, the seat cushion S1 may be provided with a pressure-receiving member, a support member, and a radio wave sensor instead of a mat 25 (refer to FIG. 6). When the support member, etc. are provided in the seat cushion S1, the upper side correspond to "the side facing the occupant, or the occupant's side" and the lower side correspond to "the side facing away from the occupant, or the side opposite to the occupant's side." The pressure-receiving member, the support member, and the radio wave sensor may each be provided on both the seat cushion S1 and the seatback S2.

In the above-described embodiments, a car seat to be installed in an automobile is given as an example of a vehicle seat, but the vehicle seat is not limited to this, and the vehicle seat may be a seat to be installed in a railcar, for example. The vehicle seat may also be installed in a vehicle other than cars such as a ship or an airplane.

The elements described in the above-described embodiments and modified examples may be implemented in combined manners as desired.

22

What is claimed is:

1. A vehicle seat including a seat cushion and a seatback, the vehicle seat comprising:
a plate-shaped pressure-receiving member configured to receive a load from an occupant seated on the vehicle seat; and
a radio wave sensor fixed to the pressure-receiving member, the radio wave sensor being configured to acquire information about the occupant by emitting radio waves toward the occupant and detecting the radio waves reflected off the occupant,
wherein the pressure-receiving member includes a plurality of first ribs that protrudes from a backside of the pressure-receiving member, which is a side facing away from the occupant, in a direction away from the occupant, and a plurality of second ribs that protrudes from the backside in a direction away from the occupant, the plurality of second ribs crossing the plurality of first ribs,
wherein the radio wave sensor includes at least one fixing part that is fixed to the pressure-receiving member, and
wherein the at least one fixing part includes a first fixing part that is fixed to a surrounded area that is surrounded by the plurality of first ribs and the plurality of second ribs on the backside.

2. The vehicle seat according to claim 1, wherein the radio wave sensor comprises a sensor part configured to acquire information about the occupant, a case that holds the sensor part, and a plurality of the first fixing parts,
wherein the plurality of the first fixing parts protrudes from a surface of the case facing the occupant,
wherein the case is opposed to the first rib and the second rib, and
wherein each one of the plurality of the first fixing parts is inserted in the surrounded area that is surrounded by the plurality of first ribs and the plurality of second ribs, and is fixed to the backside.

3. The vehicle seat according to claim 2, wherein the pressure-receiving member includes a plurality of surrounded areas, and each first fixing part is fixed to a different surrounded area.

4. The vehicle seat according to claim 3, wherein the pressure-receiving member includes at least one surrounded area provided at each of the left and right sides of a center equidistance from right and left edges of the pressure-receiving member.

5. The vehicle seat according to claim 1, wherein the pressure-receiving member and the radio wave sensor are provided at the seatback.

6. The vehicle seat according to claim 5, wherein the radio wave sensor is disposed at a lower part of the pressure-receiving member.

7. The vehicle seat according to claim 1, further comprising an attaching wire for attaching the pressure-receiving member to a frame of the vehicle seat,
wherein the attaching wire includes a pair of extended parts that extends in a direction perpendicular to a left-right direction, the pair of extended parts supporting the pressure-receiving member, and
wherein the surrounded area is provided between the pair of extended parts in the left-right direction.

8. The vehicle seat according to claim 1, wherein the fixing part is fixed to the pressure-receiving member by a screw.

9. The vehicle seat according to claim 1, wherein the pressure-receiving member comprises a center portion located at the center of the pressure-receiving member in a left-right direction and left and right side portions located respectively on left and right sides of the center portion, wherein the radio wave sensor is attached to a side portion of the pressure-receiving member.

10. The vehicle seat according to claim 9 further comprising:
a support member that support the pressure-receiving member from the backside thereof, the support member being configured to change the shape of the pressure-receiving member,
the support member including:
a first plate-shaped member;
a second plate-shaped member that moves toward or away from the first plate-shaped member in a perpendicular direction that is perpendicular to the left-right direction; and
a flexible arch member which has one end fixed to the first plate-shaped member and another end fixed to the second plate-shaped member, the arch member being configured to bend and jut out toward an occupant side and pushing the pressure-receiving member toward the occupant when the second plate-shaped member moves toward the first plate-shaped member.

11. The vehicle seat according to claim 10, wherein the pressure-receiving member, the support member, and the radio wave sensor are provided at the seatback.

12. A vehicle seat including a seat cushion and a seatback, the vehicle seat comprising:
a plate-shaped pressure-receiving member that receive a load from an occupant seated on the vehicle seat;
a support member that supports the pressure-receiving member from a side facing away from the occupant, the support member being configured to change the shape of the pressure-receiving member; and
a radio wave sensor that acquire information about the occupant by emitting radio waves toward the occupant and detecting the radio waves reflected off the occupant;
wherein the support member includes:
a first plate-shaped member;
a second plate-shaped member that moves toward or away from the first plate-shaped member in a perpendicular direction that is perpendicular to the left-right direction; and
a flexible arch member which has one end fixed to the first-plate-shaped member and another end fixed to the second plate-shaped member, wherein the arch member is configured to bend and jut out toward an occupant side and push the pressure-receiving member toward the occupant side when the second plate-shaped member moves toward the first plate-shaped member;
wherein the radio wave sensor is attached to a side, facing away from the occupant side, of the first plate-shaped member or the second plate-shaped member.

13. A vehicle seat according to claim 12, further comprising a sensor orientation changing mechanism that change an orientation of the radio wave sensor depending on the position of the radio wave sensor in the perpendicular direction.

14. The vehicle seat according to claim 13, wherein the first plate-shaped member and the second plate-shaped member are movable in the perpendicular direction, and

wherein the sensor orientation changing mechanism is configured to change the orientation of the radio wave sensor when one of the first plate-shaped member and the second plate-shaped member on which the radio wave sensor is disposed move in a specific direction, the sensor orientation changing mechanism causes the orientation of the radio wave sensor to change in a direction opposite to the specific direction.

15. The vehicle seat according to claim 14, wherein the support member further comprises a support member ascent/decent mechanism configured to move the first plate-shaped member and the second plate-shaped member together in the perpendicular direction.

16. The vehicle seat according to claim 13, wherein the pressure-receiving member, the support member, and the radio wave sensor are provided at the seatback,
wherein the radio wave sensor is provided at the first plate-shaped member, and
wherein the sensor orientation changing mechanism changes the orientation of the radio wave sensor downward when the first plate-shaped member moves upward.

17. The vehicle seat according to claim 13, wherein the pressure-receiving member, the support member, and the radio wave sensor are provided at the seatback,
wherein the radio wave sensor is provided at the first plate-shaped member, and
wherein the sensor orientation changing mechanism changes the orientation of the radio wave sensor upward when the first plate-shaped member moves downward.

18. The vehicle seat according to claim 13, further comprising a controller configured to detect the position of the radio wave sensor by making use of a historical data of an operation of a support member ascent/descent mechanism.

19. A method for manufacturing a vehicle seat comprising a seat cushion and a seatback, the method comprising:
providing a plate-shaped pressure-receiving member configured to receive a load from an occupant seated on the vehicle seat, the pressure-receiving member comprising:
a plurality of first ribs that protrudes from a backside of the pressure-receiving member, which is a side facing away from the occupant, in a direction away from the occupant; and
a plurality of second ribs that protrudes from the backside in a direction away from the occupant, the plurality of second ribs crossing the plurality of first ribs,
providing a radio wave sensor configured to acquire information about the occupant by emitting radio waves toward the occupant and detecting the radio waves reflected off the occupant, the radio wave sensor comprising at least one fixing part, and
fixing the radio wave sensor to the pressure-receiving member by fixing the at least one fixing part to the pressure-receiving member,
wherein the at least one fixing part includes a first fixing part fixed to a surrounded area that is surrounded by the plurality of first ribs and the plurality of second ribs on the backside.

* * * * *